United States Patent
Galili et al.

(10) Patent No.: US 11,083,488 B2
(45) Date of Patent: Aug. 10, 2021

(54) INSERTION GUIDE

(71) Applicant: XACT ROBOTICS LTD., Caesarea (IL)

(72) Inventors: Ben Galili, Haifa (IL); Ofer Arnold, Ma'ale Tzviya (IL); Simon Sharon, Hof Carmel (IL); Daniel Glozman, Kfar Adumim (IL)

(73) Assignee: XACT ROBOTICS LTD., Caesarea (IL)

( * ) Notice: Subject to any disclaimer, the term of this patent is extended or adjusted under 35 U.S.C. 154(b) by 178 days.

(21) Appl. No.: 15/531,435

(22) PCT Filed: Nov. 28, 2015

(86) PCT No.: PCT/IL2015/051158
§ 371 (c)(1),
(2) Date: May 28, 2017

(87) PCT Pub. No.: WO2016/084092
PCT Pub. Date: Jun. 2, 2016

(65) Prior Publication Data
US 2017/0258489 A1    Sep. 14, 2017

Related U.S. Application Data

(60) Provisional application No. 62/085,518, filed on Nov. 29, 2014.

(51) Int. Cl.
*A61B 17/34* (2006.01)
*A61B 34/20* (2016.01)
(Continued)

(52) U.S. Cl.
CPC .......... *A61B 17/3403* (2013.01); *A61B 10/04* (2013.01); *A61B 34/20* (2016.02);
(Continued)

(58) Field of Classification Search
CPC ................ A61B 17/3403; A61B 10/04; A61B 2034/2055; A61B 2034/2059;
(Continued)

(56) References Cited

U.S. PATENT DOCUMENTS 3,835,854 A * 9/1974 Jewett ................ A61M 25/0113
604/159
4,160,451 A * 7/1979 Chittenden ........ A61M 25/0113
604/159
(Continued)

FOREIGN PATENT DOCUMENTS

CN        20309019 U      7/2013
CN        203662950 U     6/2014
(Continued)

OTHER PUBLICATIONS

Supplementary European Search Report in corresponding European Application No. 15862947.7 dated Jun. 29, 2018.
(Continued)

*Primary Examiner* — Theodore J Stigell
(74) *Attorney, Agent, or Firm* — The Roy Gross Law Firm, LLC; Roy Gross

(57) ABSTRACT

A device for insertion of a flexible needle or other such instrument into a tissue, incorporating a collapsible support guide which supports that part of the needle which has not yet penetrated the tissue, preventing it from buckling, and an arrangement which pulls the needle from its proximal end to provide sufficient force for the penetration process. The collapsible support guide can be a pair of flexible strips connected along their length and enclosing the needle along its uninserted length in order to support it, with a mechanism at the distal end of the device to peel the strips from the needle as it is inserted. Insertion can be achieved by a pair of rollers engaging and advancing the strips distally. Alternatively, a telescopic support tube can be used to support the
(Continued)

needle, the tube collapsing telescopically as the needle is inserted, to maintain clearance above the needle.

20 Claims, 20 Drawing Sheets

(51) Int. Cl.
    *A61B 10/04* (2006.01)
    *A61M 25/01* (2006.01)
    *A61M 39/02* (2006.01)
    *A61N 1/372* (2006.01)
    *A61B 17/00* (2006.01)
    *A61M 25/00* (2006.01)

(52) U.S. Cl.
    CPC ........ *A61M 25/0113* (2013.01); *A61M 39/02* (2013.01); *A61N 1/372* (2013.01); *A61B 2010/045* (2013.01); *A61B 2017/00991* (2013.01); *A61B 2017/3409* (2013.01); *A61B 2034/2055* (2016.02); *A61B 2034/2059* (2016.02); *A61M 2025/0008* (2013.01); *A61M 2025/0166* (2013.01)

(58) Field of Classification Search
    CPC .... A61B 2010/045; A61B 2017/00991; A61B 2017/3409; A61B 2017/3405; A61B 2017/3411; A61M 25/0113; A61M 39/02; A61M 2025/008; A61M 2025/0166; A61N 1/372
    See application file for complete search history.

(56) References Cited

U.S. PATENT DOCUMENTS

| | | | |
|---|---|---|---|
| 4,863,429 A * | 9/1989 | Baldwin | A61M 5/1454 604/135 |
| 5,779,623 A | 7/1998 | Bonnell | |
| 6,228,039 B1 | 5/2001 | Binmoeller | |
| 7,822,458 B2 | 10/2010 | Webster, III et al. | |
| 2002/0091358 A1 * | 7/2002 | Klitmose | A61M 5/14566 604/131 |
| 2003/0199908 A1 * | 10/2003 | Boecker | A61B 5/14546 606/181 |
| 2003/0212411 A1 | 11/2003 | Jansen et al. | |
| 2006/0229641 A1 | 10/2006 | Gupta et al. | |
| 2008/0294003 A1 | 11/2008 | Honda et al. | |
| 2008/0319387 A1 * | 12/2008 | Amisar | A61M 25/0111 604/95.04 |
| 2008/0319397 A1 | 12/2008 | MacAluso | |
| 2009/0062817 A1 | 3/2009 | Suzuki et al. | |
| 2010/0249706 A1 * | 9/2010 | Clemente | A61M 5/14244 604/154 |
| 2012/0071752 A1 | 3/2012 | Sewell et al. | |
| 2015/0327939 A1 | 11/2015 | Kokish et al. | |

FOREIGN PATENT DOCUMENTS

| | | |
|---|---|---|
| EP | 983021 A2 | 3/2000 |
| WO | 98/49943 A2 | 12/1998 |
| WO | 2014098766 A1 | 6/2014 |
| WO | 2015/052719 A1 | 4/2015 |

OTHER PUBLICATIONS

Translation of Office Action dated Oct. 29, 2019, in correspnding Japanese Application No. 2017-528175.
Translation of Office Action dated Mar. 3, 2020 in corresponding Chinese Application No. 2015800749427.
PCT Search Report for International Application No. PCT/IL2015/051158 dated Mar. 27, 2016, 5 pp.
PCT Written Opinion for International Application No. PCT/IL2015/051158 dated Mar. 27, 2016, 5 pp.
PCT Preliminary Report on Patentability for International Application No. PCT/IL2015/051158 dated May 30, 2017, 6 pp.

* cited by examiner

INSERTION GUIDE

FIELD OF THE INVENTION

The present invention relates to the field of insertion of needles and other thin medical tools, and especially to devices for preventing the medical tool from buckling during insertion.

BACKGROUND

Many routine treatments employed in modern clinical practice involve percutaneous insertion of needles, catheters and other thin medical tools, for biopsy, drug delivery and other diagnostic and therapeutic procedures. The aim of an insertion procedure is to place the tip of an appropriate medical instrument safely and accurately in a target region, which could be a tumor, lesion, organ or vessel. Examples of treatments requiring insertion of a needle, or another similar medical tool, include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

Such medical tools (e.g., needles) are generally thin walled, of small diameter and mostly very long. Due to these characteristics, and because of the force needed to penetrate the patient's skin (approx. 10 N), it may be difficult to cause the needle to penetrate the patient's skin from the proximal end of the needle without the needle buckling under the force. The same problem may apply should the needle encounter a hard object in its travel, such as a bone.

In co-pending PCT application number PCT/IL2014/050891, for "Needle Steering by Shaft Manipulation" having a common inventor with the present application, there is described a device for the insertion of a needle into a patient, in which the needle is held remotely from its proximal end and pulled via a friction based mechanism. Such a device may prevent buckling, but it is complex in construction, and does not easily enable the use of disposable sterilized needle packs. Furthermore, pulling the needle from its proximal end by means of a friction drive may not provide sufficient force to overcome the penetration forces described hereinabove.

A friction drive generally requires applying radial forces on the needle, which could cause the needle to yield. As the trend in biopsy needles is for reduction of the needle wall thickness, this could become a significant issue.

In U.S. Pat. No. 7,822,458 to R. J. Webster III et al, for "Distal Bevel Tip Needle Control Device and Algorithm", there is described a method of percutaneously steering a surgical needle into a patient's tissue. One embodiment shows a pair of drive wheels pulling the needle into the patient's skin from its distal end, this embodiment having the same disadvantages as that of PCT/IL2014/050891. A second embodiment uses a telescopic guide, but has the disadvantage that because of the lead screw used in order to advance the needle, the height of the mechanism is maintained at its fixed full dimension, which hinders its use, for instance, within the limited bore of a CT system.

There therefore exists a need for a new insertion device, which overcomes disadvantages of prior art devices.

The disclosures of each of the publications mentioned in this section and in other sections of the specification, are hereby incorporated by reference, each in its entirety.

SUMMARY OF THE INVENTION

The present disclosure describes methods and apparatus for the mechanical insertion of a flexible needle or any other thin long instrument or object, into soft medium (e.g., tissue) by use of a collapsible support guide which supports that part of the needle which has not yet penetrated the medium, preventing it from buckling, yet does not impede the continuous insertion process. Different implementations of the devices described in this disclosure include:

(i) use of a flexible support guide, such as a pair of flexible strips connected along their length and enclosing the needle along at least a part of the needle's length. The strips are adapted to peel away from the needle as it is inserted, and this enables the needle to be inserted by advancing it from its proximal end in order to ensure that sufficient force can be applied for the penetration process;

(ii) use of a telescopic support tube which supports the needle and prevents that part of it outside of the patient's skin from buckling, and yet which collapses telescopically as the needle is inserted such that the height of the device does not impede use in limited spaces such as the bore of a CT system.

For the first implementation (i) described herewithin using a flexible support guide, a number of propulsion methods can be used in order to push or pull the needle-support guide assembly by its proximal end, into the patient's body, as follows:

(a) The proximal end of the guide is pulled down via a pulling mechanism, such as by cables or straps;

(b) The guide itself is perforated and two or more rollers in the lower part of the assembly have protrusions that engage the perforations of the guide and pull the guide itself distally toward the patient's body.

(c) The guide is shaped like a rack with teeth throughout at least part of its length, and its teeth mesh with corresponding gear teeth positioned at the lower part of the assembly.

(d) A friction based mechanism, in which the guides have a coarse outer surface and a pair of oppositely facing pulleys are pressed against them. The pulleys themselves may also be coarse.

(e) An array of piezo-electric drivers are mounted on one or more sides of the needle or the guide, such that their drive elements make contact with the needle or the guide respectively, and their activation propels the needle or guide distally.

For the second implementation (ii) described herewithin, the preferred propulsion method is by use of a cable distally pulling the proximal end of the telescopic assembly with its encased needle.

There is thus provided in accordance with an exemplary implementation of the devices described in this disclosure, a device for insertion of a tool, comprising:
(i) a guide member having an opening adapted to allow passage of the tool therethrough,
(ii) a propulsion mechanism configured to advance the tool through the opening in the direction of an insertion site, and
(iii) a buckling prevention mechanism configured to support the tool along at least a portion of its length while it is advanced in the direction of the insertion site,
wherein the device is configured such that its height relative to the insertion site decreases as the tool is advanced in the direction of the insertion site.

Such a device may further comprise a head element to which the tool is coupled at its proximal region. In such a case, the propulsion mechanism may include the buckling prevention mechanism and comprise:
(i) a pair of flexible strips connected along at least part of their length and having a central channel therebetween adapted to receive and support the tool, the pair of strips being coupled at its proximal region to the head element, and (ii) a pair of rollers disposed on either side of the pair of flexible strips, and interacting therewith such that counter-rotation of the pair of rollers causes the pair of flexible strips to move between the pair of rollers, wherein upon the tool being received within the central channel, the pair of flexible strips and the tool are connected by means of the head element, such that counter-rotation of the rollers in an appropriate direction pulls the pair of flexible strips and the tool towards the pair of rollers. Each roller of the pair of rollers may then comprise a plurality of protrusions arranged along its circumference, the plurality of protrusions being adapted to engage with a corresponding plurality of holes formed along the length of each strip of the pair of flexible strips. The pair of flexible strips may be connected on at least one side of the central channel adapted to receive the tool. Additionally, they may be not connected in a region of the central channel adapted to receive the tool. Such devices with rollers may further comprise a separating feature adapted to direct each strip of the pair of flexible strips around one of the pair of rollers. This separating feature may be simply the unconnected distal ends of the pair of flexible strips, each of the unconnected distal ends being wound around an associated roller of the pair of rollers. As an alternative, each roller of the pair of rollers may comprise a plurality of ridges arranged along its circumference, the ridges being adapted to engage with corresponding ridges formed in the pair of flexible strips.

In any of the above described devices, the central channel may include weakened sections along its length to facilitate the winding of each strip of the pair of flexibles strip around its associated roller. According to different implementations, the insertion device may comprise two separate units adapted to be connected to and disconnected from each other, each unit comprising:
(i) one strip of the pair of strips,
(ii) one roller of the pair of rollers, and
(iii) at least a portion of the guide member.

In yet other implementations of the above described devices, the buckling prevention mechanism may comprise a telescopic tube. Such a telescopic tube implementation may further comprise a head element to which the tool is coupled at its proximal region, wherein the telescopic tube is attached between the head element and the guide member. In either of such cases, the device may further comprise at least one gripping member connected to the telescopic tube, the at least one gripping member being configured to receive the tool and to support it as it advances in the direction of the insertion site. The tool may be enclosed within the telescopic tube. Furthermore, the head element may be moved towards the guide member by means of a cable attached between the head element and the guide member. Such a cable may be wound around a pulley attached to the guide member.

In such devices for insertion of a tool, the propulsion mechanism may comprise one or more piezo-electric actuators.

In any of the above described devices, the opening may further comprise a constraining mechanism configured to be adjusted according to the dimensions of the tool, at least a portion of the constraining mechanism being disposed within the opening. Such a constraining mechanism may comprise at least two portions disposed opposite each other, and wherein at least one of the at least two portions is adapted to be moved towards another of the at least two portions. The constraining mechanism may then further comprise a tightening screw.

Yet further implementations of the above described devices may further comprise an encoder configured to determine the position of the tool. Such an encoder may be an optical encoder configured to determine the position of the tool by one or more of sensing markings on the tool and sensing features on one or more components of the buckling prevention mechanism.

Additional examples of the devices described above may comprise two separate units adapted to be connected to and disconnected from each other, each unit comprising:
(i) at least a portion of the guide member,
(ii) at least a portion of the propulsion mechanism, and
(iii) at least a portion of the bucking prevention mechanism.

Furthermore, the tool may comprise one or more of: a needle, a cannula, a catheter, an introducer, a port, a fluid delivery tube or an electrode rod.

There is further provided in accordance with an alternative implementation of the devices of the present disclosure, an assembly for insertion of a tool, comprising:
(i) an insertion module comprising:
  (a) a guide member having an opening adapted to allow passage of the tool therethrough,
  (b) a propulsion mechanism configured to advance the tool through the opening in the direction of an insertion site, and
  (c) a buckling prevention mechanism configured to support the tool along at least a portion of its length during its advance in the direction of the insertion site,
(ii) a housing configured to receive the insertion module, and
(iii) an actuation mechanism configured to activate the propulsion mechanism.

In such an insertion assembly, the insertion module may be configured such that its height relative to the insertion site decreases as the tool advances in the direction of the insertion site. The insertion module may further comprise a head element to which the tool is coupled at its proximal region. Furthermore, the propulsion mechanism may include the buckling prevention mechanism and may comprise:
(i) a pair of flexible strips connected along at least part of their length and having a central channel therebetween adapted to receive and support the tool, the pair of strips being coupled at its proximal region to the head element, and
(ii) a pair of rollers disposed on either side of the pair of flexible strips, and interacting therewith such that counter-rotation of the pair of rollers causes the pair of flexible strips to move between the pair of rollers,
wherein upon the tool being received within the central channel, the pair of flexible strips and the tool are connected by means of the head element, such that counter-rotation of the rollers in an appropriate direction pulls the pair of flexible strips and the tool towards the pair of rollers. In such circumstances, each roller of the pair of rollers may comprise a plurality of protrusions arranged along its circumference, the plurality of protrusions being adapted to engage with a corresponding plurality of holes formed along the length of each strip of the pair of flexible strips. Furthermore, the distal ends of the pair of flexible strips may be unconnected, each of the unconnected distal ends being wound around an associated roller of the pair of rollers.

According to different implementations, the insertion module may comprise two separate units adapted to be connected to and disconnected from each other, each unit comprising:
(i) one strip of the pair of strips,
(ii) one roller of the pair of rollers, and
(iii) at least a portion of the guide member.

The buckling prevention mechanism in any of the alternative implementations of the devices of the present disclosure, may comprise a telescopic tube, in which case the buckling prevention mechanism may further comprise at least one gripping member connected to the telescopic tube, the gripping member being configured to receive the tool and to support it as it advances in the direction of the insertion site. In these alternative implementations too, the propulsion mechanism may comprise one or more piezo-electric actuators. Additionally, they may further comprise an encoder configured to determine the position of the tool. The tool itself may comprise one or more of: a needle, a cannula, a catheter, an introducer, a port, a fluid delivery tube or an electrode rod. Furthermore, a first portion of the actuation mechanism may be coupled to the housing, and a second portion of the actuation mechanism may be coupled to the guide member of the insertion module. In such devices, a locking mechanism may be configured to lock the insertion module within the housing. The locking mechanism may comprise:

(i) a rotating member coupled to the insertion module, and
(ii) one or more slits formed in the housing,
wherein rotation of the rotating member such that at least a portion of the rotating member enters at least one of the one or more slits, locks the insertion module within the housing.

Furthermore, in the above described insertion assemblies, the housing may comprise one or more coupling elements adapted to couple the housing to an automated insertion device, the automated insertion device including at least a controller. Also, the insertion module may comprise two separate units adapted to be connected to and disconnected from each other, each unit comprising:
(i) at least a portion of the guide member,
(ii) at least a portion of the propulsion mechanism, and
(iii) at least a portion of the bucking prevention mechanism.

According to yet further implementations of the devices of this disclosure, there is provided a device for insertion of a tool, comprising:
(i) a pair of flexible strips connected along at least part of their length and having a central channel therebetween adapted to receive the tool, and
(ii) a pair of rollers disposed on either side of the pair of flexible strips, and interacting therewith such that counter-rotation of the pair of rollers causes the pair of flexible strips to move between the pair of rollers,
wherein upon the tool being received within the central channel, the pair of flexible strips and the tool are secured together at an end remote from the pair of rollers, such that counter-rotation of the rollers in an appropriate direction pulls the pair of flexible strips and the tool towards the pair of rollers.

In such yet further implementations, each roller of the pair of rollers may comprise a plurality of protrusions arranged along its circumference and adapted to engage with corresponding plurality of holes formed along the length of each strip of the pair of flexible strips. The pair of flexible strips may be connected on at least one side of the central channel adapted to receive the tool, and may be not connected in a region of the central channel. Such devices may further comprise a holder member configured to secure together the pair of flexible strips and the tool. They may also have a guide member, the guide member including:
(i) one or more cavities adapted to accommodate the pair of rollers, and
(ii) an opening adapted to allow passage of the tool therethrough.

In that case, the opening may further comprise a constraining mechanism configured to be adjusted according to the dimensions of the tool, at least a portion of the constraining mechanism being disposed within the opening. The constraining mechanism may then comprise at least two portions disposed opposite each other, and wherein at least one of the at least two portions is adapted to be moved towards another of the at least two portions.

Such yet further implementations may further comprise a separating feature adapted to direct each strip of the pair of flexible strips around one of the pair of rollers. Such a separating feature may comprise unconnected distal ends of the pair of flexible strips, each of the unconnected distal ends being wound around an associated roller of the pair of rollers. Alternatively, it may comprise a pair of structural edges, each being disposed sufficiently close to an associated roller that each flexible strip is directed by one of the edges around that roller disposed close to the edge. Alternatively, the pair of rollers may be disposed within a guide member, and each of the structural edges are then the edges of a component of the guide member.

In any of such yet further implementations, the central channel may include weakened sections along its length to facilitate the winding of each flexible strip around its associated roller. Furthermore, the distance between two adjacent protrusions of the plurality of protrusions may be larger than the distance between two adjacent holes of the plurality of holes. The external surfaces of the pair of rollers and the external surfaces of the pair of flexible strips may alternatively be roughened such that the interaction between them is achieved by means of friction. The tool may comprise a tip, and the insertion device may further comprise a protecting element configured to prevent the tip from contacting an internal surface of the central channel as the tool is advanced in the direction of the insertion site. The protecting element may be inserted within the central channel, and it may comprise a hollow tube. Alternatively and additionally, it may be coupled to at least a portion of the insertion device externally to the central channel. Finally, in any of these yet further implementations, the insertion device may comprise two separate units adapted to be connected to and disconnected from each other, each unit comprising:
(i) one strip of the pair of strips, and
(ii) one roller of the pair of rollers.

Additionally, alternative implementations of devices of the present disclosure may further involve an assembly for insertion of a tool, comprising:
(i) an insertion module comprising:
  (a) a pair of flexible strips connected along at least part of their length and having a central channel therebetween adapted to receive the tool, and
  (b) a pair of rollers disposed on either side of the pair of flexible strips, and interacting therewith such that counter-rotation of the pair of rollers causes the pair of flexible strips to move between the pair of rollers,
  wherein upon the tool being received within the central channel, the pair of flexible strips and the tool are secured together at an end remote from the pair of rollers, such that counter-rotation of the rollers in an appropriate direction pulls the pair of flexible strips and the tool towards the pair of rollers,
(ii) a housing configured for receiving the insertion module, and
(iii) an actuation mechanism configured to rotate the pair of rollers.

In such an assembly, a first portion of the actuation mechanism may be coupled to the housing. Also, the insertion module may comprise a second portion of the actuation mechanism. Any of such assemblies may further comprise a locking mechanism configured to lock the insertion module within the housing. In such a case, the locking mechanism may comprise:

(i) a rotating member coupled to the insertion module, and
(ii) one or more slits formed in the housing, wherein rotation of the rotating member such that at least a portion of the rotating member enters at least one of the one or more slits locks the insertion module within the housing.

The above described assemblies may further comprise a separating feature adapted to direct each strip of the pair of flexible strips around one of the pair of rollers, and that separating feature may itself comprise unconnected distal ends of the pair of flexible strips, each of the unconnected distal ends being wound around an associated roller of the pair of rollers. Additionally, such assemblies may further comprise:

(i) a front leading element coupled to the insertion module, and
(ii) a back leading element coupled to the housing, wherein the front and back leading elements are configured to receive therebetween one of the unconnected ends of the pair of strips after the one of the unconnected ends is wound around its associated roller of the pair of rollers.

According to further implementations of such assemblies, the housing may comprise one or more coupling elements adapted to couple the housing to an automated insertion device, the automated insertion device including at least a controller. Furthermore, the insertion module may comprise two separate units adapted to be connected to and disconnected from each other, each unit comprising:

(i) one strip of the pair of strips, and
(ii) one roller of the pair of rollers.

Finally, according to yet another implementation of the devices of the present disclosure, there is provided a device for insertion of a tool, comprising:

(i) a head element to which the tool is attached at a proximal region of the tool,
(ii) an end guide element through which the tool is delivered to an insertion site, and
(iii) a telescopic tube attached between the head element and the end guide element, wherein as the telescopic tube collapses, the head element is moved towards the end guide element and the tool advances towards the insertion site. In such devices, the head element may be moved towards the end guide element by means of a cable attached between the head element and the end guide element. That cable may be wound around a pulley attached to the end guide element. Any of these other implementations may further comprise at least one gripping element configured to receive the tool and to support it as it advances in the direction of the insertion site. The tool may be enclosed within the telescopic tube.

It is to be understood that the terms proximal and distal as used in this disclosure have their usual meaning in the clinical arts, namely that proximal refers to the end of a device or object closest to the person or machine inserting or using the device or object and remote from the patient, while distal refers to the end of a device or object closest to the patient and remote from the person or machine inserting or using the device or object.

It is also to be understood that although the examples used throughout this disclosure relate to a device for insertion of a needle, the device is not meant to be limited to use with a needle but is understood to include insertion of any long thin tool, medical or other, which may undergo buckling if pushed or pulled from its proximal end without any support means, including a needle, port, introducer, catheter (e.g., ablation catheter), cannula, surgical tool, fluid delivery tool, or any other such insertable tool.

BRIEF DESCRIPTION OF THE DRAWINGS

The present invention will be understood and appreciated more fully from the following detailed description, taken in conjunction with the drawings in which:

in FIG. 5A the motors operate on the flexible strips, and in FIG. 5B directly on the needle.

in FIG. 15A the locking mechanism is in an open state; in FIG. 15B the locking mechanism is in a closed state.

DETAILED DESCRIPTION

Figure 1:
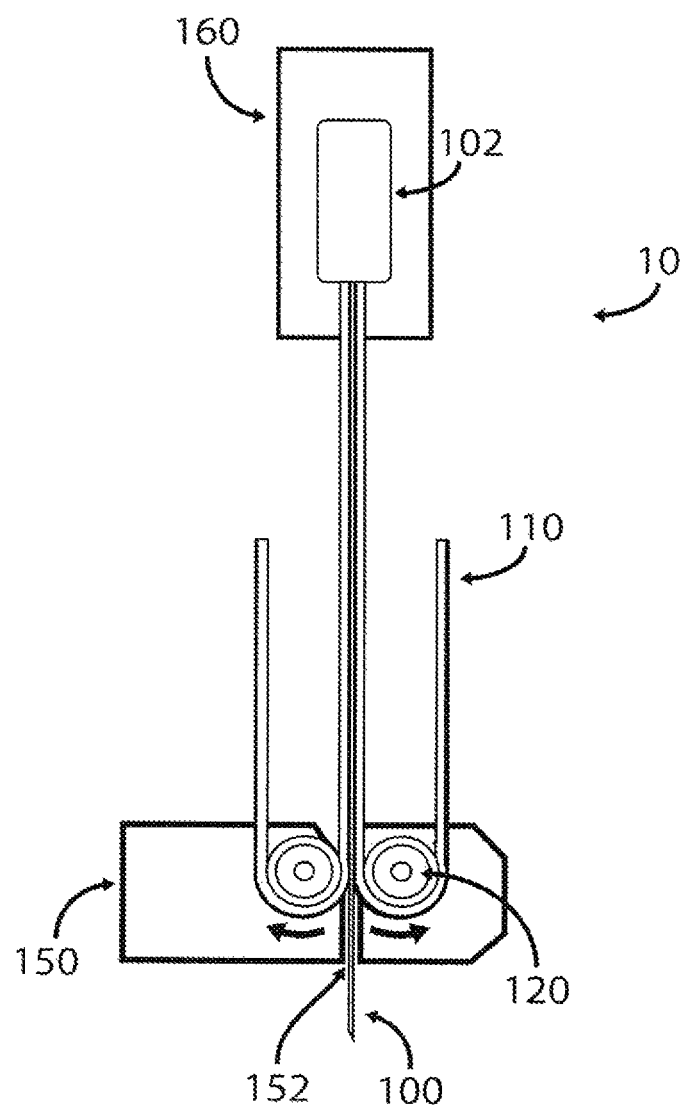
FIG. 1 shows schematically a cross-sectional view of a first exemplary implementation of an insertion device of the present disclosure.

Reference is first made to FIG. 1, which shows schematically a cross-sectional view of a first exemplary implementation of the needle insertion devices described in this disclosure. FIG. 1 shows an insertion device 10, with a needle (or any other thin insertable element) 100 held between a pair of flexible strips 110, of supporting medium. The strips are held together conveniently by means of an adhesive, welding, geometric lock mechanisms such as a snap fit mechanism, or any other suitable attachment means, and the needle 100 is held between the two strips 110 down a thin channel running down the center of the coupled strips 110. The distal end of the insertion device 10 comprises a holder 150 in which a pair of rollers 120 are disposed. The holder 150 further includes an opening 152 for guiding the needle 100 distally towards the patient's body. The rollers 120 are positioned within the holder 150 such that they contact the strips 110, and as the rollers 120 counter-rotate, the double strip-needle assembly moves between the rollers 120. The rollers 120 may be positioned within cavities formed within the holder 150, the inner walls of the cavities being a close fit to the outer surfaces of the rollers 120, such that as the flexible strip-needle assembly passes between the rollers 120, the needle 100 is able to proceed through the opening 152 beyond the rollers 120, while each one of the flexible strips 110 is peeled away from the needle 100 on either side of the rollers 120. The needle then emerges from the double roller assembly bereft of its flexible strip covering, and ready for insertion into the patient's body. In some implementations, a "knife-edge" (not shown in FIG. 1) or the straight corner of one of the holder elements may be positioned such that it causes the peeling of the flexible strips 110 away from the needle 100 and around the rollers. In order to assist in this action, the forward (i.e., distal) ends of the twin flexible strips 110 may be left unconnected so that each can peel away freely around its own roller 120. The insertion device 10 may even be supplied with each unconnected strip end partially wound around its roller 120, or even attached thereto, or just directed each towards a distal point on the circumference of its roller 120, such that rotation of the rollers 120 causes the strips 110 to peel away from the needle 100 without the need for an "knife-edge" or the like to separate the strips 110 from each other and from the needle 100.

The strips 110 may be paper-based or plastic-based, or made of any other material capable of supporting the needle 100 along its length, thereby preventing it from buckling, but at the same time being flexible enough to curve around the rollers 120 and away from the needle 100. Such materials may be, for example, Polyethylene terephthalate (PET), Polyurethane (PU) or rubberized fabric. At their proximal ends, the flexible strips 110 may be attached to the needle head 102, or to a needle head holder 160, which encloses and grips the needle head 102, such that as the rollers 120 counter-rotate and move the double strip-needle assembly towards the patient's skin, the proximal end of the flexible strips 110 pulls with it the needle head 102, and thus the needle 100, distally towards the insertion point in the patient's skin. The propulsion of the needle 100 from its proximal end is a unique feature which provides the needle 100 with sufficient force to enable it to overcome any obstacles in its insertion path, whether at the skin entry point or further down during the insertion process.

An encoder may optionally be disposed adjacent to the strips 110, so that the position of the strips, and hence the insertion position of the needle 100 can be determined, such as by a controller or a processor (not shown) receiving the output signals of the encoder. By this means, the medical personnel are able to track the progress of the insertion depth of the needle 100. The encoder can be, for example, an optical encoder, which can either count features on the strip 110, such as the strip drive holes or ridges, as will be shown hereinbelow in FIGS. 3 and 4, or can detect markings on the needle itself.

The insertion device 10 may be a stand-alone device, or it may be part of an insertion assembly/system. In case the insertion device 10 is a stand-alone device, it may further comprise an actuation mechanism, e.g., motor and gears, for rotating the rollers 120 and thus moving the needle 100 towards (and into) the patient's body. In the case that the insertion device is part of an insertion assembly/system, it may be configured to be coupled to an external actuation mechanism.

Figure 2:
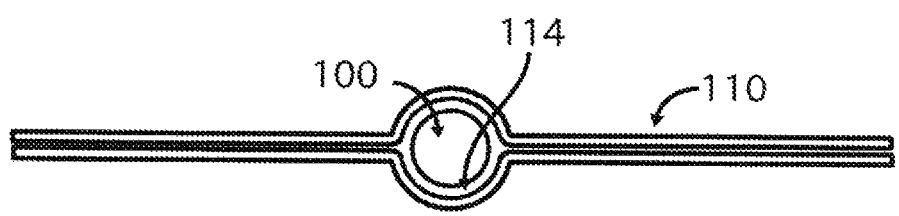
FIG. 2 shows an axial cross-section view of a needle enclosed between the two guiding strips of the insertion device of FIG. 1.

Reference is now made to FIG. 2, which is an axial cross-section view of the two strips 110 of the insertion device of FIG. 1 and the needle 100 enclosed therebetween. As shown, the two flexible strips 110 are coupled together along their width, except in the region where they envelop the needle 100 at their center line. Each strip 110 has a groove 114 running along its centerline, providing the strip with an "omega-like" traverse cross-section, such that when the strips 110 are coupled together, e.g., using an adhesive, the longitudinal grooves 114 of the two strips 110 form together a hollow tube, or a channel, which receives and encloses the needle 100. The strips 110 may be coupled to the needle head 102 (not shown in FIG. 2, but visible in FIG. 1) or secured to the needle holder 160 (not shown in FIG. 2) together with the needle head 102.

Figure 3:
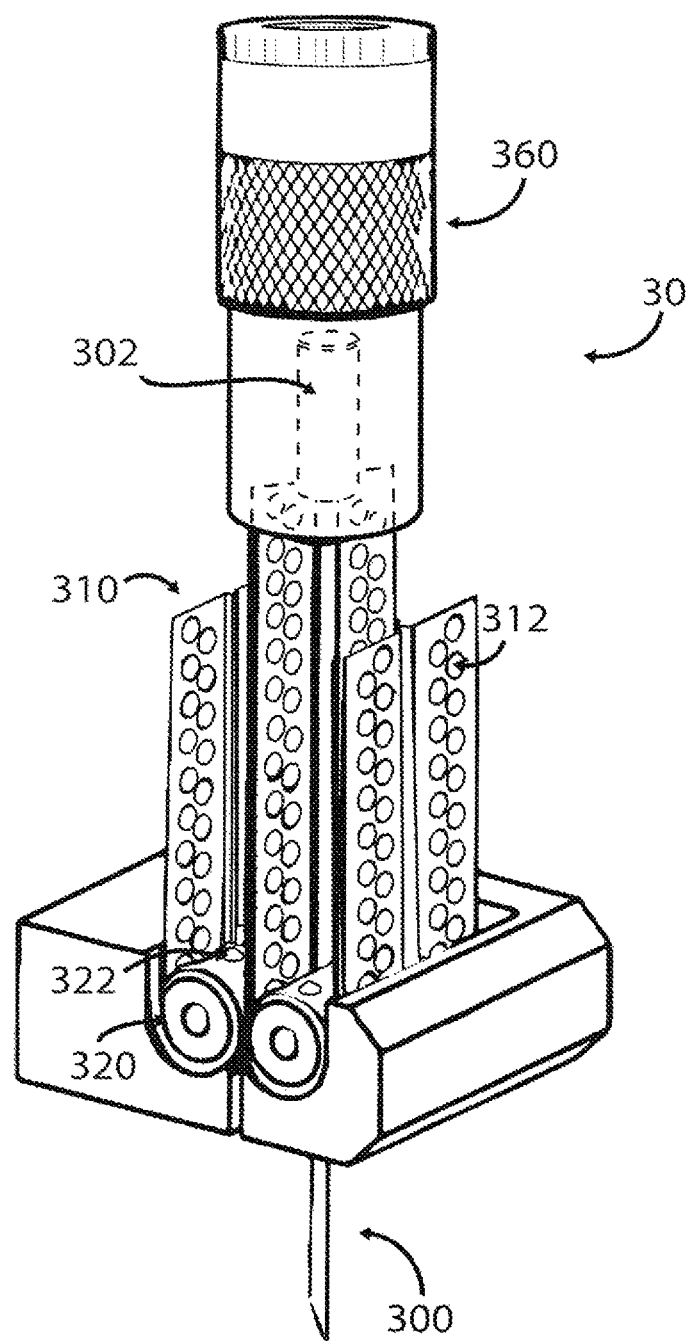
FIG. 3 is an isometric view showing schematically an implementation of a flexible strip device with perforations running along the length of the strips.

As mentioned above, a number of methods are available in order to propel the needle distally into the patient's body. Reference is now made to FIG. 3, which is an isometric view showing schematically a first implementation of the flexible tape device 30. In this implementation the flexible strips 310 have perforations 312 running along at least a portion of the length of the strips 310 and on either side of the needle position along the centerline. As these perforations 312 engage with corresponding protrusions (or -teeth) 322 on the rollers 320, and as the rollers 320 counter-rotate in the appropriate direction, the double strip-needle assembly is forced in a distal direction. The proximal ends of the strips 310 are attached to the needle head 302 and/or to the needle head holder 360, such that as the strips 310 move distally towards the patient's body, their proximal ends pull the needle towards the patient. More specifically, counter-rotation of the rollers 320 pulls downwardly the coupled strips 310 via a "timing belt-like" mechanism comprised of the rollers' protrusions and the strips' holes. The strips' pull forces then react with the needle head holder 360 which pushes the needle 300 downwardly from the needle head 302. This force can be substantially higher than that which could be obtained if the rollers 320 were to grip the needle 300 itself by frictional forces, and pull it down from its distal end. As mentioned above, the entire device 30 can be a stand-alone device or it can be part of an insertion system, e.g., it can be mechanically (e.g., robotically) held to align the needle 300 relative to the patient.

Figure 4:
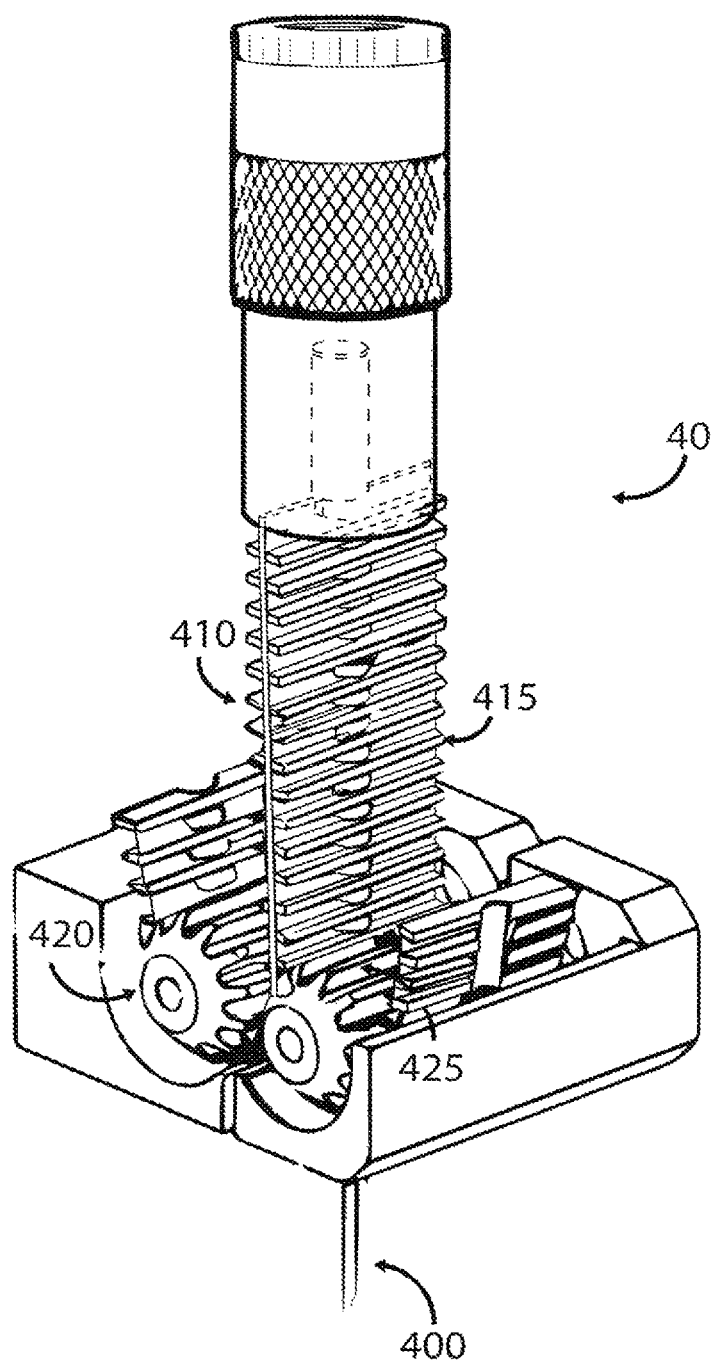
FIG. 4 is an isometric view showing schematically an implementation of a flexible strip device with ridges running along the length of the strips.

Reference is now made to FIG. 4, which illustrates schematically an alternative method of locomotion for the flexible strips. In this implementation the rollers 420 are configured as gears, and the strips 410 are formed with ridges 415 on their outer edges and across at least a part of their width. The ridges 415 mesh with the teeth 425 of the rollers/gears 420, similarly to a rack and pinion mechanism, and as the rollers/gears 420 counter-rotate, the double strip-needle assembly is forced in a distal direction. The attachment method of the flexible strips 410 at their proximal ends may be the same as that described for the implementation of FIG. 3.

Although the implementations shown in FIGS. 3 and 4 provide the double strip-needle assembly with optimum, slip-free propulsion force, it is also possible to use conventional friction forces to propel the assembly. In such an embodiment the surfaces of the rollers and the external surfaces of the flexible strips have a friction interface, such as roughened surfaces on one or on both, so that rotation of the rollers causes the flexible strips to move accordingly.

In order to provide sterilized operation of the device, a number of options are available. The flexible strips may be supplied with the needle installed as a complete sterile assembly, ready for mounting into the roller assembly. Alternatively, the roller assembly may also be part of the supplied device, making the entire device a disposable one-time use device. In further embodiments, the roller assembly, with the strips inserted thereto devoid of any needle, may be provided as a one-time use disposable unit, such that the user can choose the needle to be installed into the double flexible strip guide. In such embodiments, the double flexible strip guide may be supplied with a thin walled introducer tube down its bore, into which the user can insert the needle, following which the introducer tube can be withdrawn and the needle left enveloped by the flexible strips guide. This enables the user to introduce the needle without unintentionally scratching or puncturing the soft material of the flexible strips, which may further result in particles of the strips' material remaining inside the needle and entering the patient's body.

Another solution for preventing the needle from scratching the inner surface of the strips may be, for example, including within the bore between the strips a short rod (i.e., shorter than the length of the bore between the strips) with a cone-shaped head, positioned at the top (proximal) end of the bore, the concave side of the cone-shaped head facing the proximal end of the bore, and thus also the incoming needle, such that when the needle is introduced into the bore, its tip encounters the bottom of the concave side of the cone-shaped rod head, and as the needle is being inserted into the bore it pushes down on the cone-shape rod head, thus pushing the entire rod downwardly until the rod falls out from the bottom (distal) end of the bore and the needle is left therein. Yet a further solution may be using an external stabilizing mechanism that is coupled to the device, or at least to the double strip-needle assembly, in order to hold it straight and prevent the strips from folding as the needle is being inserted into the bore, thus preventing the needle from scratching/puncturing the strips' inner surface. Once the needle is positioned properly within the bore between the strips, the external stabilizing member may be removed. Such a mechanism may be disposable and provided with the device, i.e., pre-assembled, and discarded after a single use.

Figure 5A:
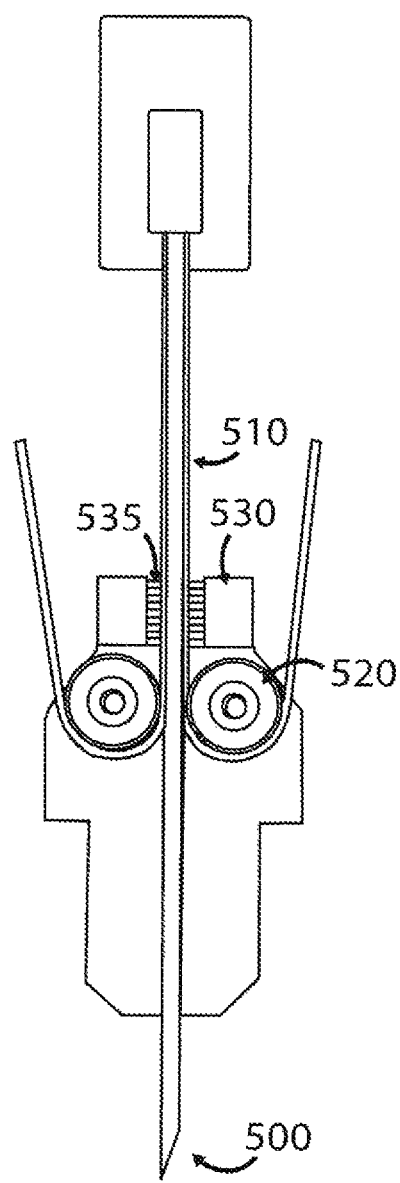
FIGS. 5A and 5B illustrate schematically an implementation in which the motion is applied to the needle by means of piezoelectric motors.
Figure 5B:
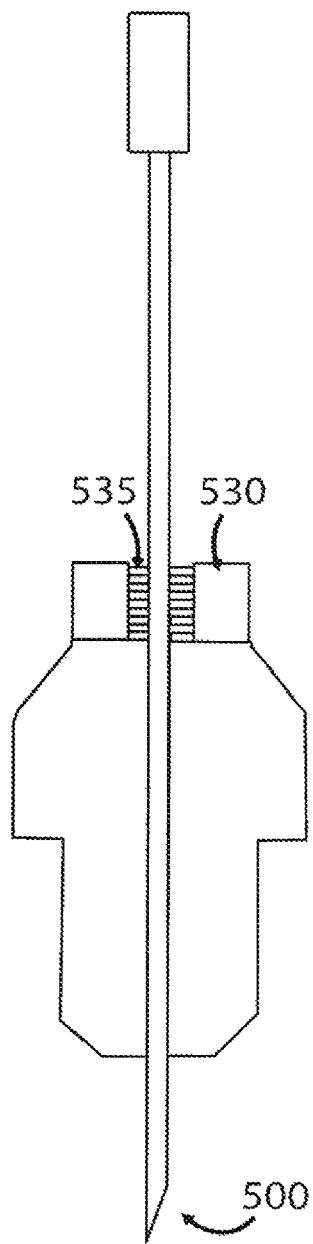

Reference is now made to FIGS. 5A and 5B, which illustrate schematically an implementation in which the motion is applied to the needle by means of piezoelectric motors. In FIG. 5A, the piezoelectric motors 530 are situated on either side of the flexible strips 510, such that as they are activated, their driver legs 535 move the strips 510 with the encased needle 500 distally towards the patient's body. In this implementation, the rollers 520 need not take part in the propulsion, and can function just in order to guide the flexible strips 510 so that they are peeled away from the needle 500. FIG. 5B shows a similar implementation except that no flexible strip is used, and the piezoelectric motors 530 operate directly on the needle 500.

Figure 6A:
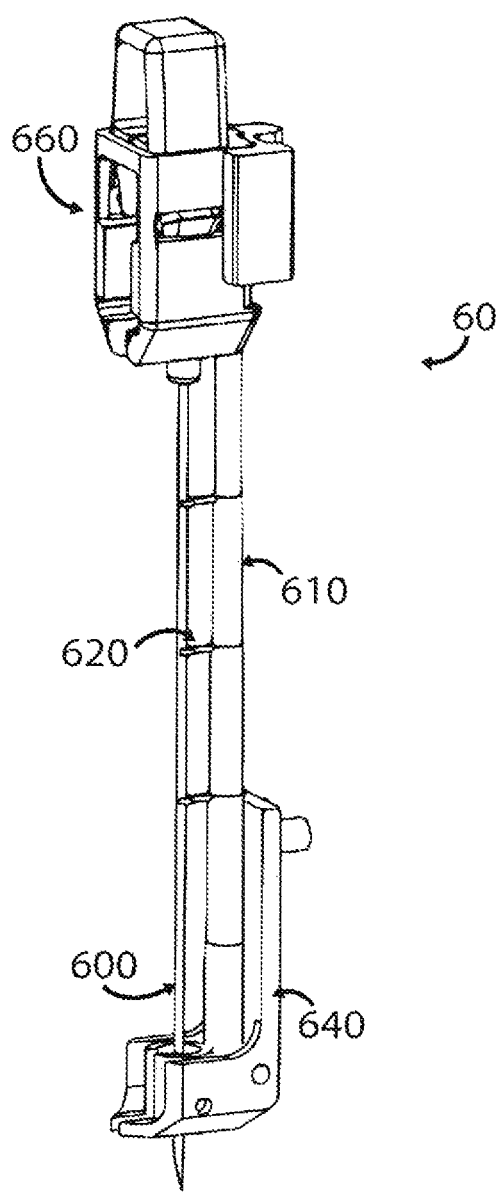
FIG. 6A illustrates schematically a further implementation of the insertion devices of the present disclosure, in which the needle is supported from buckling by means of a telescopic tube having gripping clamps in each of its levels.
Figure 6B:
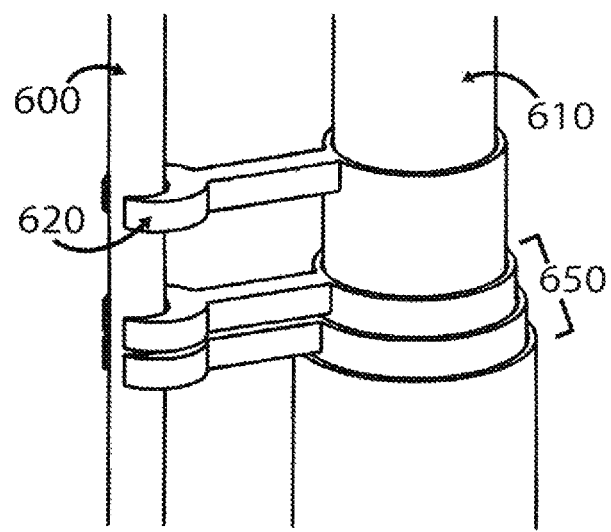
FIG. 6B is a close up view of the needle clamps of the device of FIG. 6A.
Figure 7:
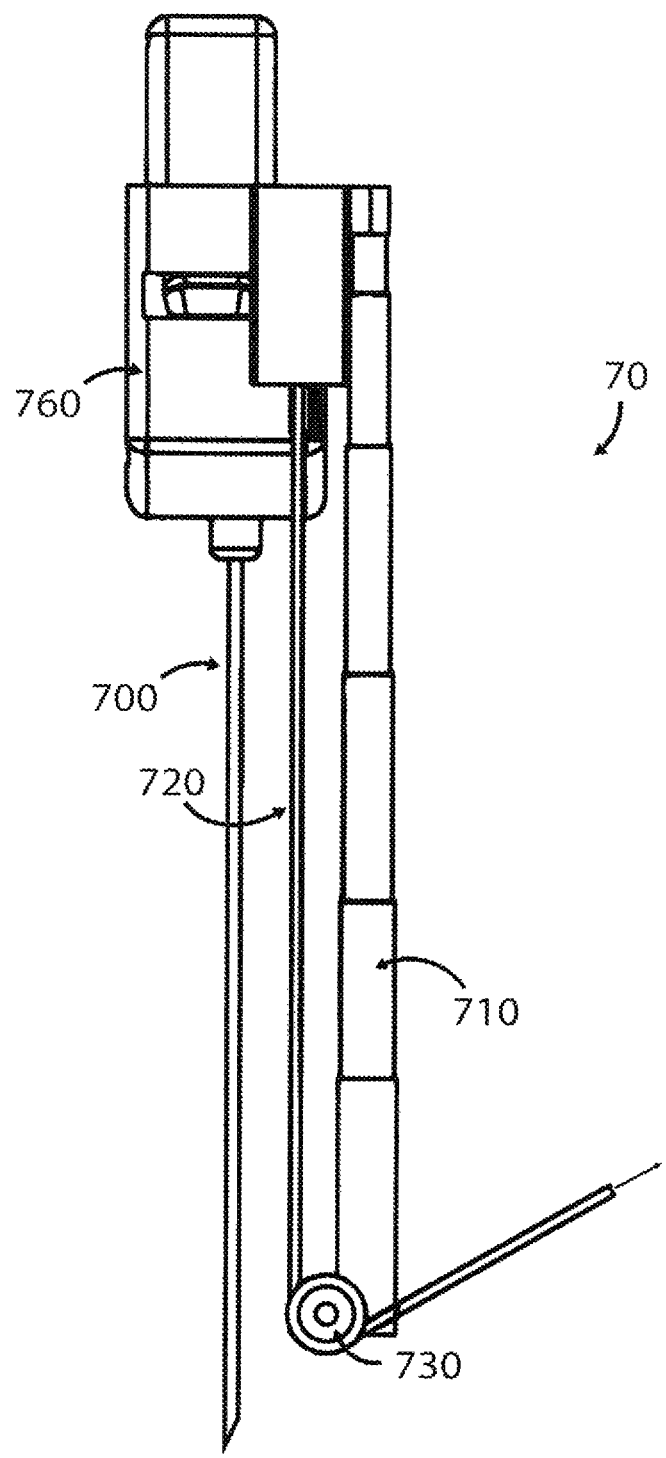
FIG. 7 shows an alternative example of a telescopic tube support device, showing a wire traction assembly for the needle head.

Reference is now made to FIGS. 6A to 7, which illustrate schematically further implementations of the insertion device of the present disclosure, in which the needle is supported from buckling by means of a telescopic tube which provides support along the length of the needle. However unlike prior art telescopic support systems, these implementations enable the height of the device to be reduced as the needle is inserted, such that they are more convenient for use in limited space situations, such as in the bore of a CT system. The needle is attached to a holder element at its proximal end, and to a needle guide at its distal end to align the correct insertion point of the needle. The telescopic tube assembly is attached between the holder element and the end guide to provide support to the needle as it is pushed (or pulled) into the patient by means of a force applied to the holder element.

FIG. 6A shows an insertion device 60 having a telescopic tube 610 attached to the needle 600 by means of clamps 620, which allow the needle to slide through them. As the holder element 660, to which the needle is attached, is pushed (or pulled) distally to insert the needle 600 into the patient's body, the telescopic tube 610, which is connected between the holder element 660 and the distal end guide 640 of the device, collapses, enabling the holder 660 to approach the distal end guide 640 as the needle 600 is inserted. The holder element 660 may be pushed down manually or it may be pushed or pulled down using various propulsion mechanisms, such as a pulley wheel and a cable, as shown below in FIG. 7. In some implementations, the needle 600 is not externally attached to the telescopic tube 610, but encapsulated therein.

Reference is now made to FIG. 6B, which is a close up view of the clamps 620 of the device shown in FIG. 6A, showing how the needle 600 can slide through the openings in the clamps 620 as the telescopic tube 610 collapses upon itself, as shown in region 650 of the telescopic tube assembly.

Reference is now made to FIG. 7, which shows a further exemplary implementation of the telescopic tube support devices shown in FIGS. 6A and 6B, showing an insertion device 70 in which the motion of the needle 700 is achieved by means of a cable 720 attached to the needle head holder 760, and passed around a pulley wheel 730 at the distal end of the telescopic tube 710, and pulled manually or by means of a motor, a hydraulic/pneumatic piston or any other suitable actuation/propulsion mechanism (not shown). By means of such a configuration, needle motion can be obtained by means of a mechanism whose length collapses together with the telescopic support guide 60, thereby overcoming the above mentioned problem of how to perform needle insertion in limited spaces, where the length of a conventional lead screw drive mechanism connected between the needle head and the distal end, for example, as described in the abovementioned U.S. Pat. No. 7,822,458, would interfere with this aim.

Reference is now made to FIGS. 8A-11C, which show an exemplary implementation of the insertion device shown in FIG. 3, i.e., a flexible strip device with perforations running along the length of the strips. In this implementation, the insertion device (which may also be referred to as "insertion module") is configured as part of an insertion assembly, which is configured for coupling to an automated insertion system (e.g., a robotic system). Such an automated insertion system may be body-mounted or may be configured for coupling to a dedicated arm connected to the patient's bed or to the imaging device (e.g., CT, MRI), if the procedure is image-guided.

Figure 8A:
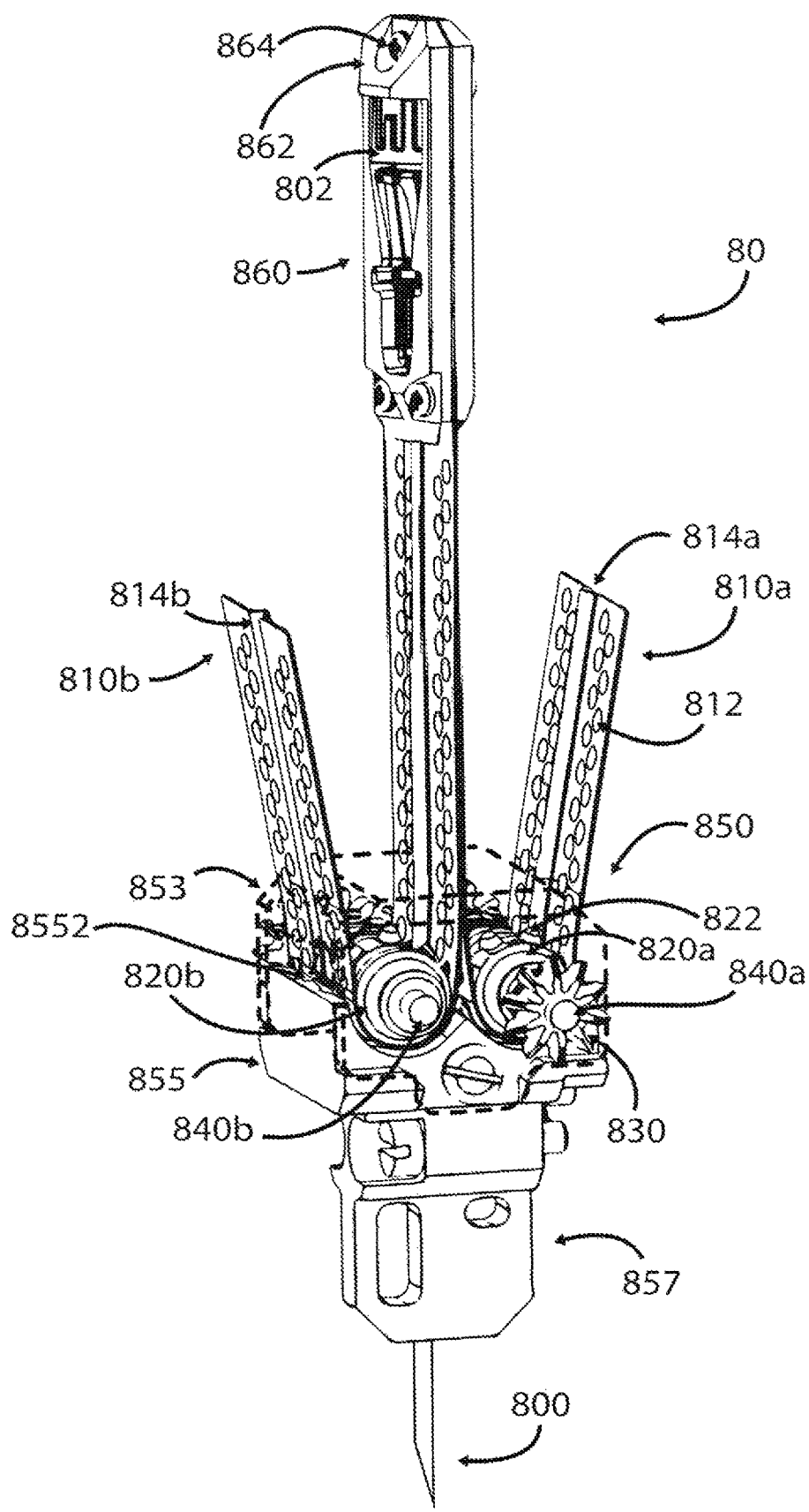
FIG. 8A shows a perspective view of an exemplary implementation of the flexible strip device with perforations running along the length of the strips of FIG. 3.

FIG. 8A shows a perspective view of an insertion module 80 comprising a needle (or any other insertable tool, such as an introducer, a catheter, etc.) 800 enclosed within a channel formed by two flexible strips 810*a*, 810*b* coupled together. In some implementations, the needle 800 is provided together with the insertion module 80, i.e., as an integral component of the insertion module, whereas in other implementations, the insertion module is configured to receive a variety of different commercially available needle types, and the needle is chosen and introduced into the insertion module by the user (e.g., nurse, physician) prior to initiating the insertion procedure.

The flexible strips 810*a*, 810*b* have perforations (or -holes) 812 running along at least a portion of their length, and a groove 814*a*, 814*b* running along their longitudinal centerline, such that when the strips are attached to each other their coupled grooves 814*a*, 814*b* form together the channel that receives and encloses the needle 800.

In some implementations, each strip 810*a*, 810*b* may include four rows of perforations 812, e.g., two rows on each side of the groove 814*a*, 814*b*, as shown in FIG. 8A. In other implementations, each strip 810*a*, 810*b* may include two rows of perforations 812, one row on each side of the groove 814*a*, 814*b*, as shown below in FIG. 9B. It can be appreciated that the arrangement of the perforations is not limited to two or four rows, and the strips may include any number of perforation rows or any other applicable perforation arrangement.

The insertion module 80 further comprises two rollers 820*a*, 820*b* having protrusions 822 thereon. The protrusions 822 are aligned with the perforations 812 of the strips 810*a*, 810*b*, such that as each roller 820*a*, 820*b* rotates, its protrusions 822 engage the perforations 812 of the corresponding strip 810*a*, 810*b*, resulting in the strips 810*a*, 810*b* being pulled down and around the rollers 820*a*, 820*b*.

The insertion module 80 may further include a bevel gear 830 mounted on the same shaft 840*a* as one of the rollers, in this case roller 820*a*, such that rotation of the bevel gear 830 causes roller 820*a* to rotate in the same direction. Counter-rotation of the second roller 820*b* is achieved via two gears mounted at the opposite end of the shafts 840*a*, 840*b*, as described below in FIG. 8B.

The shafts 840*a*, 840*b*, and the rollers 820*a*, 820*b* may be enclosed within a holder 850, which may include a shaft (or -axes) holder portion 853, a strip guide portion 855 and a needle guide portion 857. The shaft holder portion 853 is configured to hold and secure the position of the shafts 840*a*, 840*b*. The strip guide portion 855 is configured to lead the strips away from the rollers as the rollers continue to rotate, and its walls may include slits 8552 that allow passage for the protrusions 822 as the rollers rotate. The needle guide portion 857 may include an elongated "tube-like" opening (not shown in FIG. 8A), which is configured to receive the needle 800 as it is pulled (or pushed) in the distal direction and the strips 810 are peeled away from the needle 800. The needle guide portion 857 also confines the needle 800 to the elongated opening and thus guides the needle 800 in the desired direction of insertion.

Figure 8B:
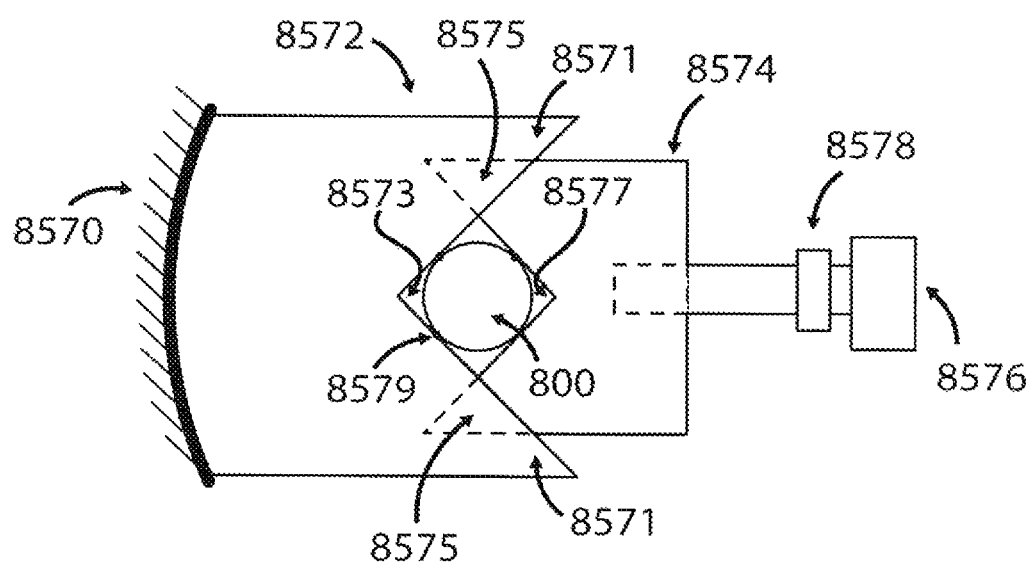
FIG. 8B shows an exemplary needle constraining mechanism.

In some implementations, in order for the insertion module 80 to be used with a variety of needle types and sizes, the elongated opening may have a diameter that is equal or slightly larger than that of the needle with the largest diameter (gauge) intended for use with the insertion module 80. In other implementations, the elongated opening may include therewithin a constraining mechanism, which can be adjusted according to the diameter of the needle being used. An exemplary constraining mechanism is shown in FIG. 8B, which is a transverse cross-sectional view of the mechanism. The constraining mechanism may include a stationary portion 8572, which is fixedly connected to the inner surface 8573 of the needle guide portion 857 of the holder 850, and a moveable portion 8574. The moveable portion 8574 may be connected to a screw (or -bolt) 8576 whose head is positioned outside the needle guide portion 857 so that it is accessible to the user. The bolt 8578 may be coupled to a stationary nut 8578, such that rotation of the bolt 8576 results in linear movement of the moveable portion 8574. In some implementations, the stationary and moveable portions may each comprise a block with two triangular edges 8571, 8575 respectively, forming therebetween a v-groove 8573, 8577 respectively, and as the moveable portion 8574 advances towards the stationary portion 8572 the triangular edges 8575 of the moveable portion 8574 fit beneath the block of the stationary portion 8572, as shown in FIG. 8B, or vice versa. In other implementations, the stationary and moveable portions may each comprise a plurality of such blocks and the triangular edges 8571, 8575 intertwine as the moveable portion 8574 advances towards the stationary portion 8572. Thus, after a needle 800 is inserted into the insertion module, the user rotates the bolt 8576 in the appropriate direction such that the moveable portion 8574 advances towards the stationary portion 8572 until there is contact between the needle 800 and the two v-grooves 8573, 8577 and the needle 800 is tangent to each of the triangular edges 8571, 8575 along a single line 8579 (shown as a dot in FIG. 8B). It can be appreciated that the constraining mechanism may include instead of the bolt 8576, or in addition to the bolt, a spring (not shown), or any other element suitable for moving/pushing the moveable portion 8574 towards the stationary portion 8572.

The axes holder portion 853, strip guide portion 855 and needle guide portion 857 may be three separate components assembled together to form the holder 850, or they may be manufactured as a single unit. In some implementations two of the three portions (e.g., the strip guide and needle guide portions) may be manufactured as one component, which is then coupled to the third portion (e.g., the axes holder portion).

The insertion module 80 may further include a needle head holder 860, which secures together the needle head 802 and the proximal end of the strips 810*a*, 810*b*. In some implementations, the needle head holder 860 may be composed of two portions 862 which are coupled together after the needle 800 is inserted into the channel between the two strips 810*a*, 810*b*, e.g., using screws, an adhesive or a latch mechanism. In some implementations, the two portions 862 of the needle head holder 860 may be fixedly secured together at their distal end, to which the proximal ends of the strips 810*a*, 810*b* are attached, and after the needle 800 is inserted into the channel between the two strips, the proximal (top) ends of the two portions 862 are joined together over the needle head 802. If intended for use in the medical field, the insertion module 80 should be a disposable single-use device, in order to prevent cross-contamination between patients. Thus, in some implementations, in order to ensure that the insertion module 80 is not reused with a new needle, the needle head holder 860 may be configured such that once it is fastened over the needle head 802, it cannot be removed from the needle head 802, or that removing the needle head holder 860 from the needle head 802 causes permanent damage to the needle head holder 860 such that it loses its functionality.

Figure 9:
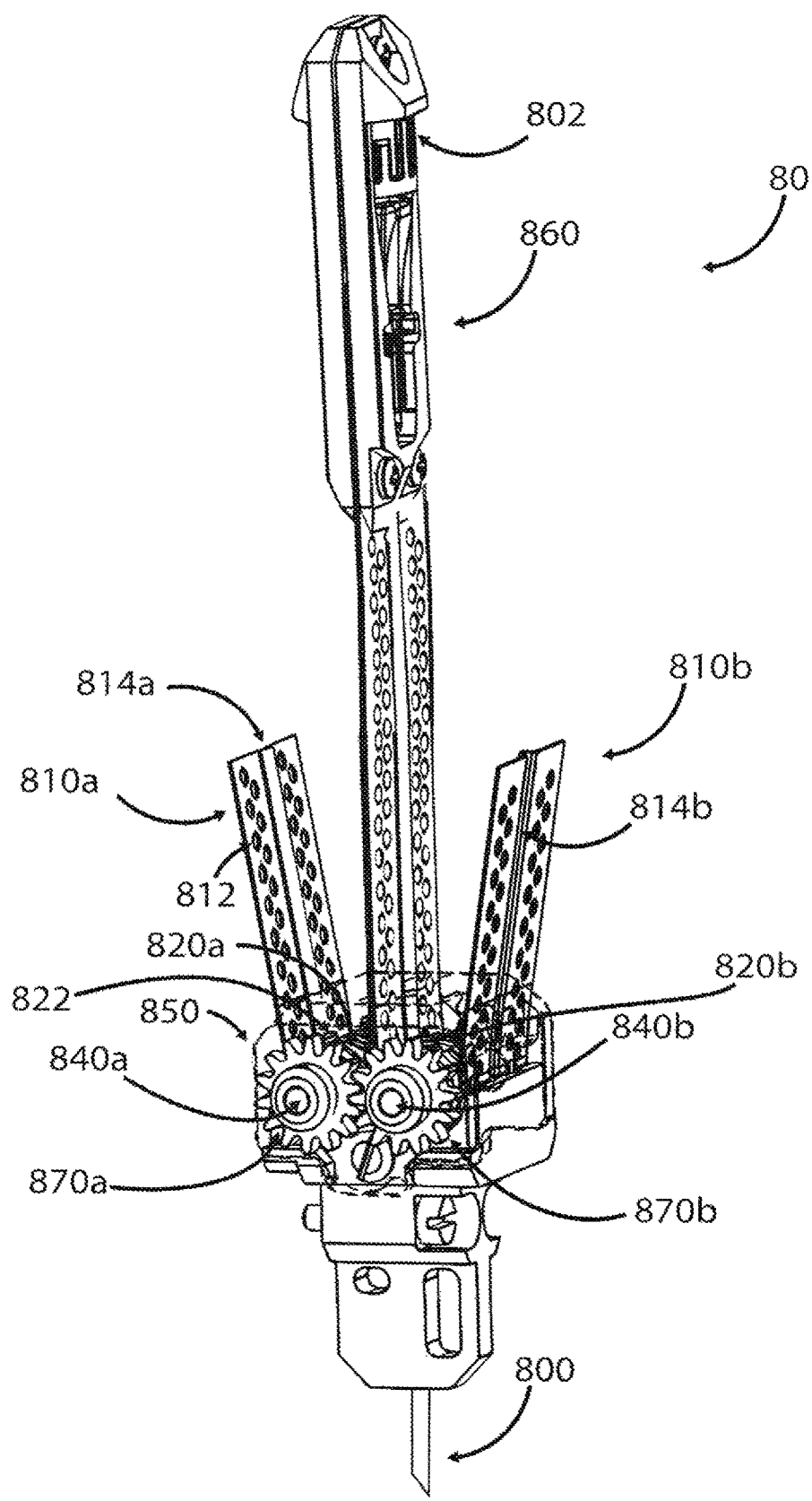
FIG. 9 shows another perspective view of the insertion device of FIG. 8A.

FIG. 9 shows another perspective view of the insertion module 80. As described above, the insertion module 80 may include a bevel gear (not shown in FIG. 9), which in this implementation is mounted on shaft 840a of roller 820a. Thus, rotation of the bevel gear 830 causes roller 820a to rotate in the same direction. The insertion module 80 further includes two gears 870a, 870b which are mounted on the roller shafts 840a, 840b respectively. The gear 870a is mounted on shaft 840a at the end opposite the end at which the bevel gear is mounted, such that rotation of the bevel gear causes rotation of the gear 870a in the same direction as the bevel gear and roller 820a. The teeth of the gear 870a mesh with the teeth of the gear 870b, causing the gear 870b to rotate in the direction opposite that of the gear 870a. Since the roller 820b is mounted on the same shaft 840b as the gear 870b, rotation of the gear 870b results in rotation of the roller 820b in the same direction as the gear 870b, i.e., in the opposite direction of the roller 820a. As the rollers 820a, 820b counter-rotate, their protrusions 822 engage the strips' perforations 812, such that the strips 810a, 810b, together with the enclosed needle 800, are pulled in the distal direction towards the patient's body. The strips 810a, 810b are then forcefully separated from one another, pulled in opposite directions and around the rollers 820a, 820b, while the needle 800 continues its translation in the distal direction and into the body of the patient.

In some implementations at least one of the gears 870a, 870b may be a ratchet gear, provided with a pawl, so that the gears can only rotate in one direction, while synchronizing or meshing the rotation of the rollers 8201, 820b. Use of a ratchet gear prevents re-use of the insertion module 80, which after one use is no longer sterile, with a new needle. It can be appreciated that the insertion module 80 may include other mechanisms to prevent its re-use, such as a non-removable needle head holder, as described above.

Figure 10A:
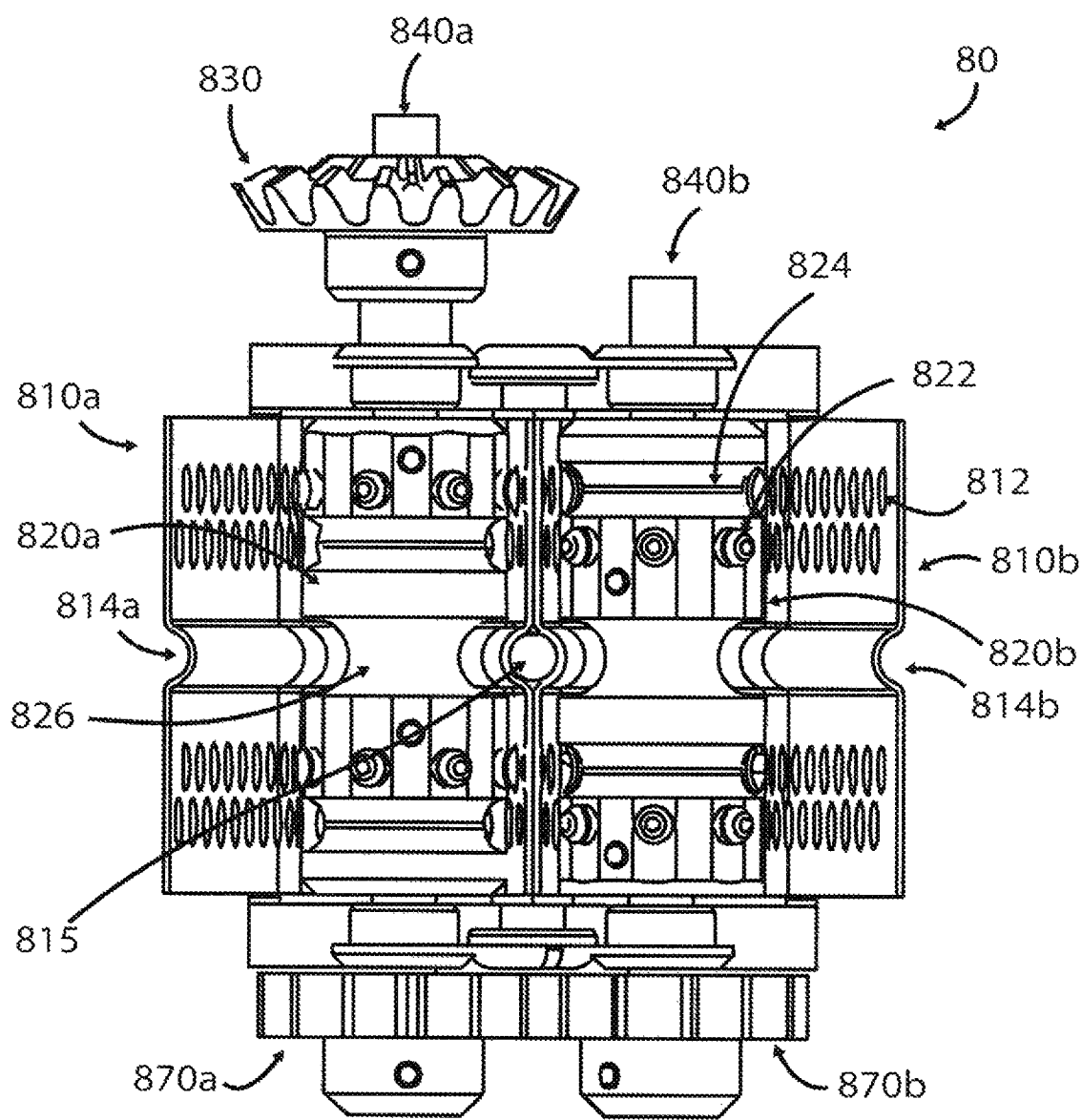
FIGS. 10A-10B are top views of two exemplary arrangements of the rollers and the strips of the insertion device of FIG. 8A.

FIG. 10A is a top view of the insertion module 80, without the needle and the needle head holder, showing an exemplary arrangement of the rollers 820a, 820b within the holder 850 (not shown in FIG. 10A). In this implementation, in order to avoid the risk of the protrusions 822 of the two rollers bumping into each other as the rollers counter-rotate, which may interrupt the insertion procedure or even cause damage to the strips or the needle, etc., the rollers 820a, 820b are positioned in opposite directions relative to each other, such that the protrusions of each roller do not face the protrusions of the other roller. Further, the protrusions 822 are disposed circumferentially around each roller, such that each roller 820a, 820b includes two "rings" of protrusions 822. In this implementation, opposite each such "ring" there is an annular groove 824 on the other roller, which allows uninterrupted passage of the protrusions 822 as the rollers 820a, 820b counter-rotate. Since the protrusions 822 do not face each other, the strips 810 in this implementation are provided with four rows of perforations 812, one row corresponding to each of the four protrusion "rings".

In some implementations, each roller 820a, 820b further includes an additional annular groove 826, which may be wider and deeper than the annular grooves 824, and disposed in the transverse center of the roller, in order to allow uninterrupted passage of the convex side of the grooves 814a, 814b running down the longitudinal center of the strips 810a, 810b, as the strips move in the distal direction and around the rollers 820a, 820b. When the strips 810a, 810b are attached (e.g., adhered) to each other, the longitudinal grooves 814a, 814b form together the channel 815 which receives and accommodates the needle therein. In some implementations, instead of the insertion module 80 including two rollers 820a, 820b each having an annular center groove 826, the insertion module 80 may include four rollers, each pair of rollers disposed on a single shaft, and spaced apart so as to allow uninterrupted passage of the convex side of the grooves 814a, 814b therebetween.

Figure 10B:
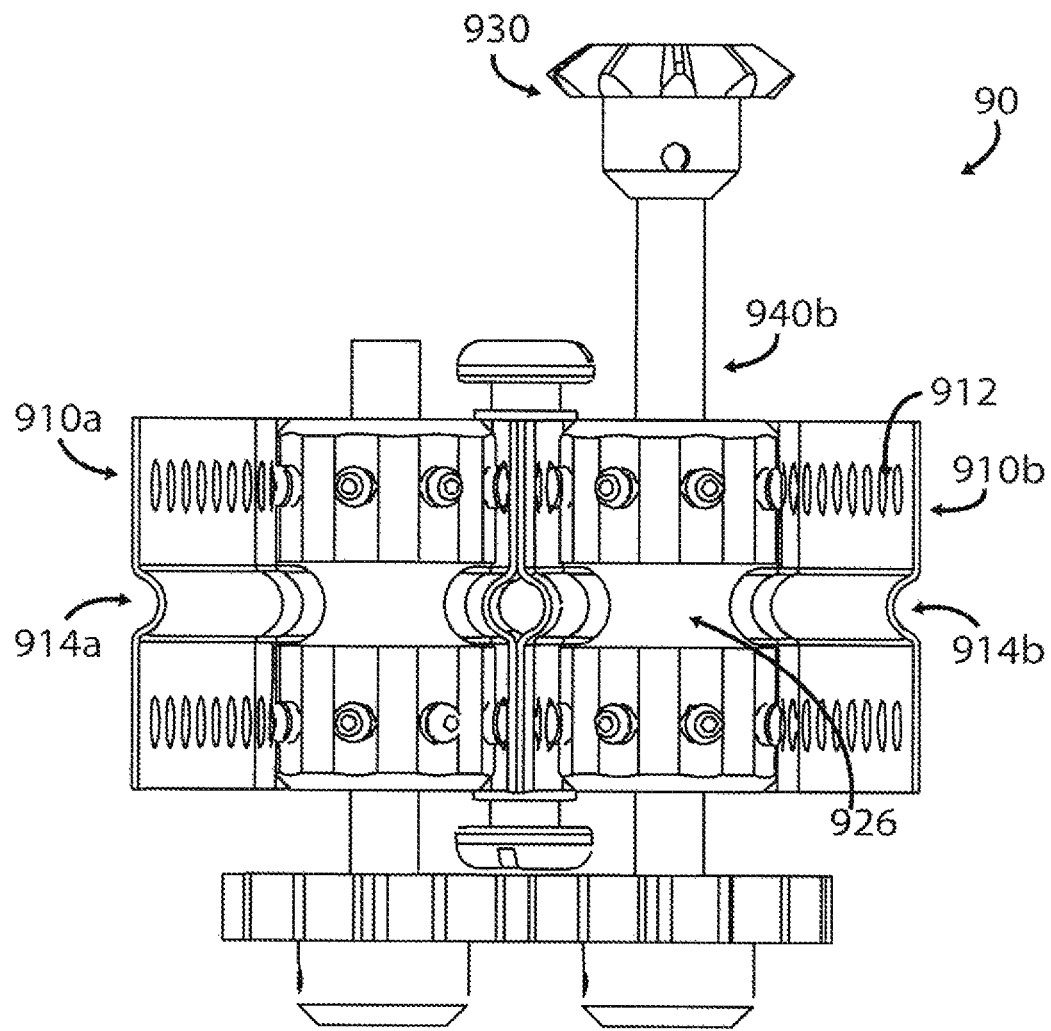

FIG. 10B is a top view showing an alternative arrangement of rollers 920a, 920b within the holder (not shown in FIG. 10B) of another exemplary insertion module 90. In this implementation, the rollers 920a, 920b are spaced apart slightly further than the rollers 820a, 820b of FIG. 10A, such that the protrusions 922 of the two rollers 920a, 920b can be disposed on the rollers such that they face each other without there being a risk of the protrusions of the two rollers 920a, 920b bumping into each other as the rollers counter-rotate. Accordingly, in this implementation each strip 910a, 910b has only two rows of perforations 912, one row on each side of the annular groove 914a, 914b.

It can be appreciated that, similarly to the implementation shown in FIG. 10A, in this implementation as well the insertion module 90 may include, instead of two rollers 920a, 920b each having an annular center groove 926, four rollers mounted two on each of the shafts 940a, 940b.

As further shown in FIG. 10B, in some implementations the bevel gear 930, the rotation of which results in rotation of the rollers 920a, 920b, may be mounted on shaft 940b.

Figure 11:
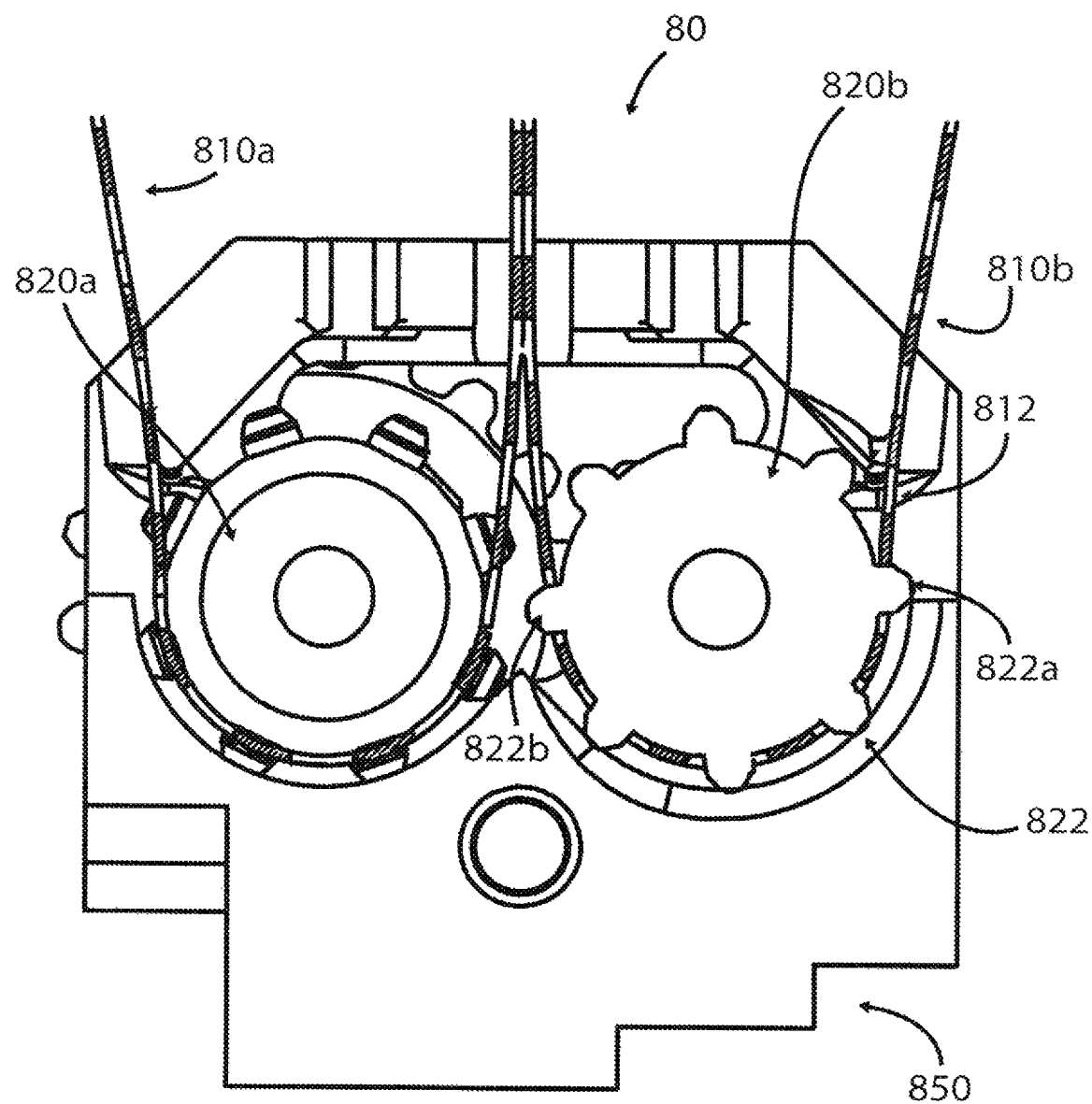
FIG. 11 is a cross-sectional view of operative interface between the rollers and the strips of the insertion device of FIG. 8A.

Reference is now made to FIG. 11, which is a cross-sectional view showing the protrusions 822 of the roller 820b as they engage the perforations 812 of strip 810b. As described above, in some implementations the protrusions of the two rollers 820a, 820b do not face each other, i.e., they are disposed in an offset relative to each other. Accordingly, the cross-sectional view of FIG. 11 depicts only the protrusions of roller 820b as they engage the perforations of strip 810b, and the interface between the protrusions of roller 820a and the perforations of strip 810a cannot be seen. However, it can be appreciated, that the description below regarding the interface between the protrusions of roller 820b and the perforations of strip 810b applies equally to the interface between the protrusions of roller 820a and the perforations of strip 810a.

In some implementations the pitch of the roller 820b may be slightly larger than the pitch of the strips 810b, i.e., the distance between two adjacent roller protrusions may be larger than the distance between two adjacent strip perforations. As a result, the load of pulling the strip falls on the last protrusion 822a that remains engaged with the strip 810b before the strip disengages from the roller 820b. This is advantageous since it ensures that the strip 810b remains tightly coupled to the roller 820b in the section between the first engaging protrusion 822b and the last engaging protrusion 822a, as the roller 820b rotates. If the distance between two adjacent protrusions 822 was smaller than the distance between two adjacent perforations 812, the load of pulling the strip 810 would fall on the first protrusion 822b that engages the strip 810b as the roller 820b rotates. This might result in the strip 810b disengaging from the roller 822b as it rotates and falling onto the internal surface of the holder 850, which may result in high friction or even damage to the strip and/or roller and interruption of the insertion procedure. Further, the friction forces may increase in case the strip 810b includes an adhesive on its internal surface for attachment to the second strip 810a, since the remains of the adhesive might cause the strip 810b to attach to the internal surface of the holder 850 after the strips are separated from each other.

Figure 12C:
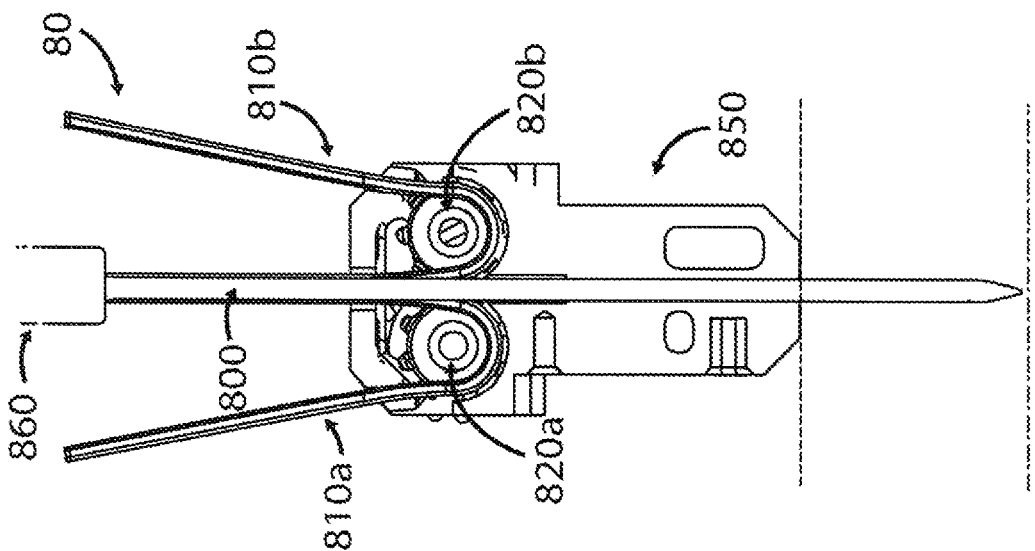
FIGS. 12A-12C are longitudinal cross-sectional views depicting three needle insertion stages using the needle insertion device of FIG. 8A.
Figure 12B:
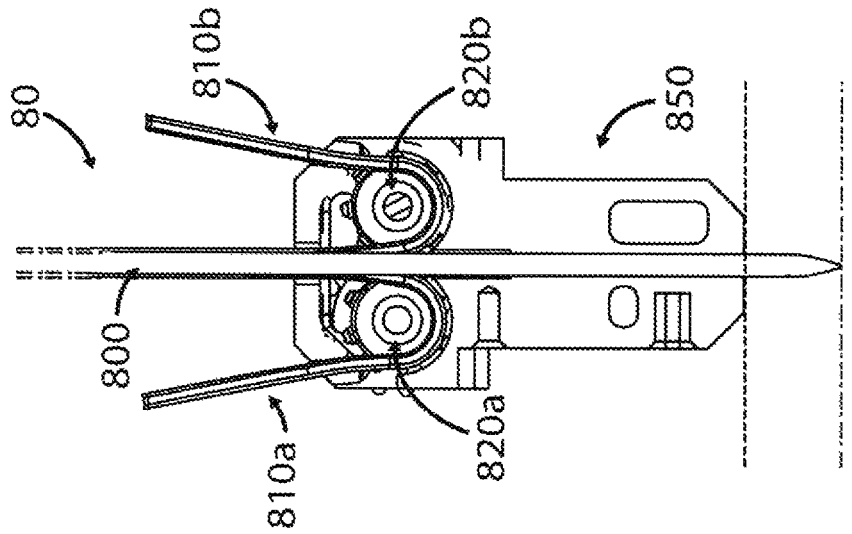
Figure 12A:
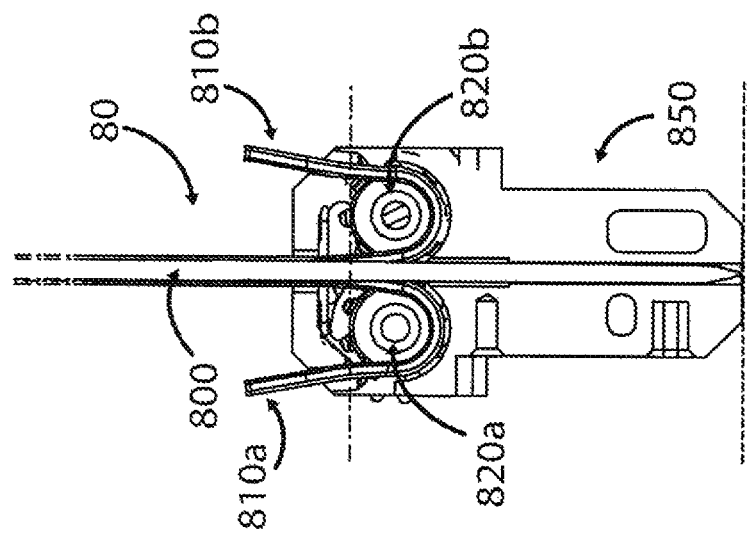

Reference is now made to FIGS. 12A-12C which show longitudinal cross-sectional views of the insertion device 80 illustrating three different stages of the needle insertion procedure.

FIG. 12A shows the insertion device 80 at its initial state, i.e., prior to initiation of the insertion procedure. In the shown embodiment, the device is supplied with the distal end of the strips 810a, 810b already wound around the rollers 820a, 820b respectively so as to ensure that the strips detach from one another and roll outwardly and away from each other, together with the counter-rotating rollers 820a, 820b. In some implementations, prior to commencement of the insertion procedure, the tip of the needle 800 is substantially aligned with the distal (bottom) end of the holder 850. In other implementations the needle tip may be slightly concealed within the holder 850 or it may slightly protrude therefrom. FIG. 12B shows the insertion device 80 after the needle 800 has been partially inserted into the patient's body, and the strips 810a, 810b have peeled further away from the needle 800 and around the rollers 820a, 820b.

FIG. 12C shows the insertion device 80 at an advanced stage of the insertion process. The needle head holder 860 is now nearing the holder 850 and the rollers 820a, 820b and the strips 810a, 810b are further peeled off the needle 800 and wound around the rollers 820a, 820b.

Figure 13:
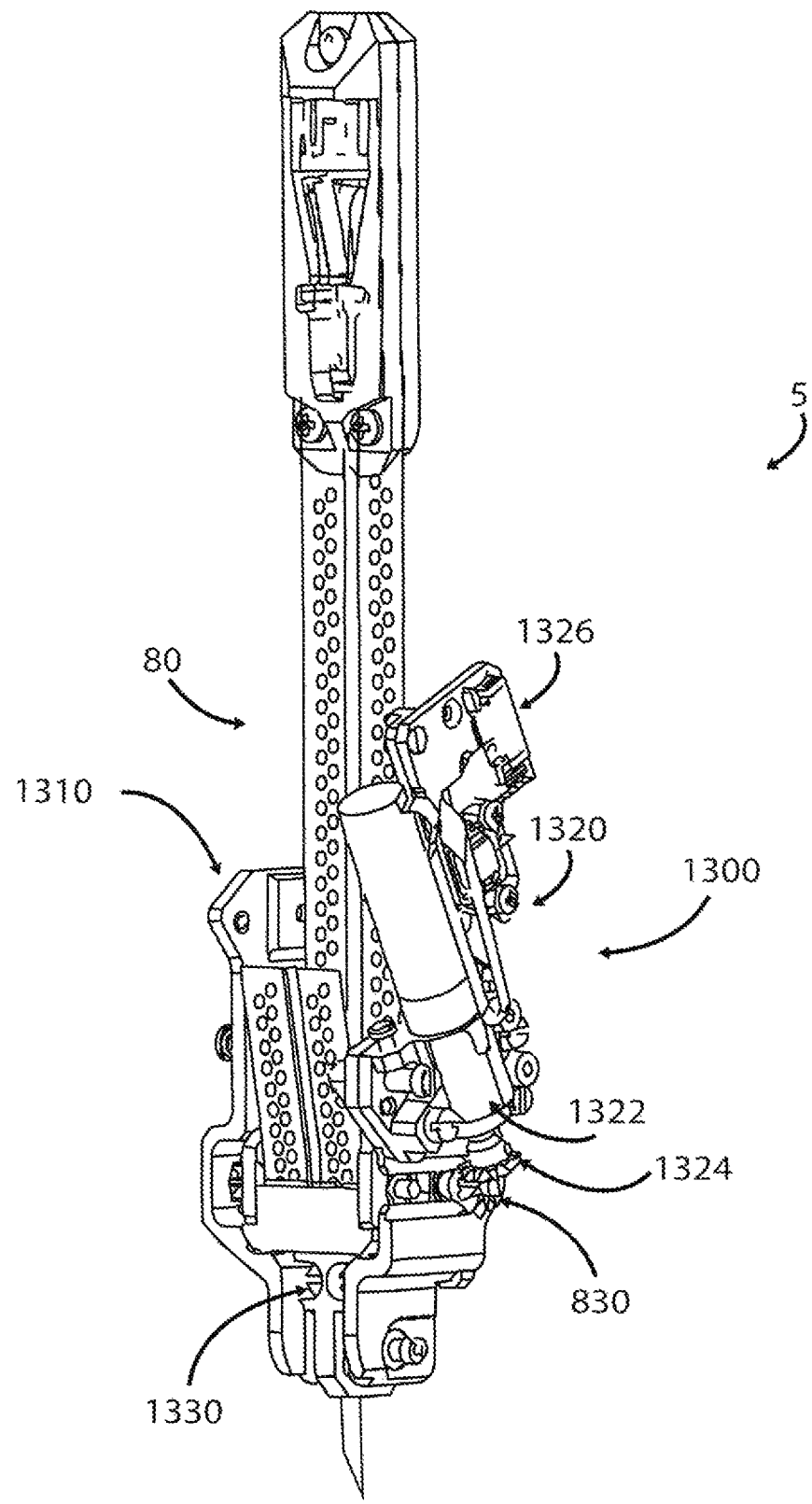
FIG. 13 shows a perspective view of an exemplary insertion assembly comprising the insertion device of FIG. 8A coupled to a robotic end effector.

Reference is now made to FIG. 13, which shows a perspective view of an insertion assembly 5 comprising the insertion module 80 coupled to a robotic end effector 1300. The end effector 1300 includes a frame (or -housing) 1310 for receiving and housing the insertion module 80, and a motor assembly 1320, which includes a geared motor 1322 (i.e., motor and planetary gear system) provided with a motor encoder (not shown) for verifying proper function of the geared motor 1322, a bevel gear 1324, and a Printed Circuit Board (PCB) 1326. After the insertion module 80 is coupled to the end effector 1300, it may be secured to the end effector 1300 using one or more screws 1330, or any other suitable securing mechanism, such as the mechanism shown hereinafter in FIGS. 15A-15B.

In some implementations, the insertion module 80 is a disposable single-use unit, and the end effector 1300 is reusable, i.e., it can be used repeatedly with new disposable insertion modules 80. In such cases the end effector 1300 is preferably an integral unit of an automated (e.g., robotic) insertion device (not shown in FIG. 13). In other implementations the end effector 1300 may be disposable and separate from the automated insertion device. In such cases the end effector 1300 and the insertion module 80 may be manufactured as a single unit.

In some implementations, the motor assembly 1320 is an integral component of the end effector 1300. In other implementations, the motor assembly 1320 may be separate from the end effector 1300 such that it is coupled to the end effector 1300 either before or after the insertion module 80 is coupled to the end effector 1300. The motor assembly 1320 actuates the insertion mechanism as follows: the geared motor 1322 rotates the bevel gear 1324, which in turn rotates the bevel gear 830 of the insertion module 80, to which it is coupled. The bevel gear 830 of the insertion module 80 then rotates the rollers (not shown in FIG. 13) of the insertion module 80, as described above with regard to FIGS. 8A and 9. It can be appreciated that any other applicable method of transferring moment from the motor assembly 1320 to the insertion module 80 may be implemented, and using coupled bevel gears 830 and 1324 is merely one exemplary method.

In case the motor assembly 1320 is an integral part of the end effector 1300, the motor assembly 1320 may be connected to the frame 1310 such that the motor assembly 1320 can be moved aside in order to allow proper coupling (and de-coupling) of the insertion module 80 to the end effector 1300. For example, the interface between the motor assembly 1320 and the frame 1310 may be in the form of a hinge, such that the motor assembly 1320 can pivot about its axis. After the insertion module 80 is introduced into the frame 1310, the motor assembly 1320 is moved back to its position such that the bevel gear 1324 is properly coupled to the bevel gear 830 of the insertion module 80. The motor assembly 1320 may be moved back to its position either manually or automatically, e.g., the motor assembly 1320 may include a projection (not shown) which is pressed (or otherwise engaged) by the insertion module 80 as it is being inserted into the frame 1310 of the end effector 1300, such that coupling the insertion module 80 to the end effector 1300 causes the motor assembly 1320 to return to its place and establish operative coupling with the insertion module 80 (e.g., between bevel gear 830 of the insertion module and bevel gear 1324 of the motor assembly 1320).

Figure 14:
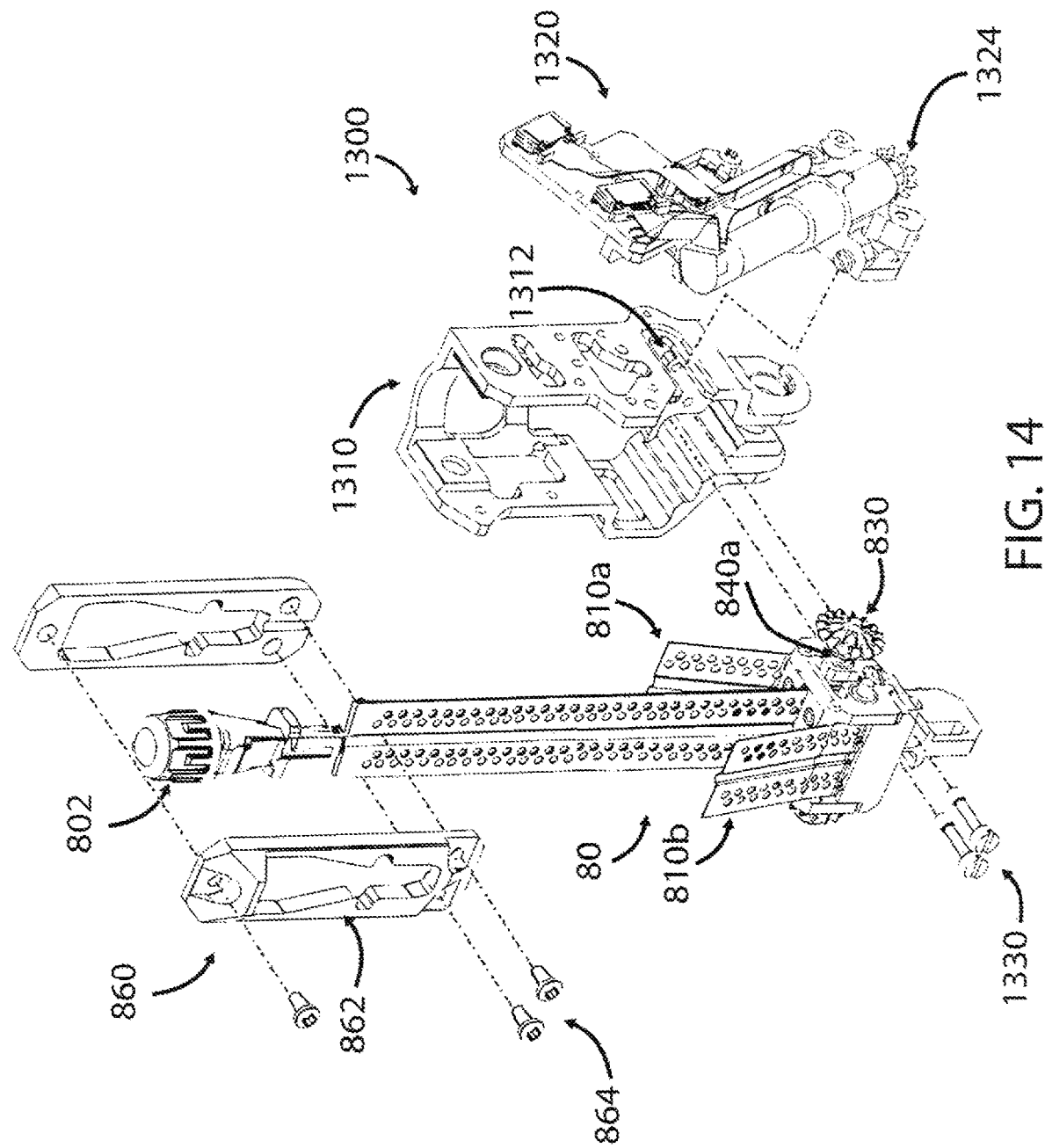
FIG. 14 is an exploded view of the insertion assembly of FIG. 13.

FIG. 14 shows an exploded view of the insertion assembly 5 of FIG. 13. Shown are the insertion module 80 with the two portions 862 of the needle head holder 860, which when connected by means of a plurality of screws 864, for example, secure together the needle head 802 and the proximal end of the strips 810a, 810b. Also shown is the end effector 1300 comprising the end effector frame 1310 and the motor assembly 1320. As previously discussed, the insertion module 80 is coupled to the end effector 1300 by inserting the insertion module 80 into the end effector frame 1310, and locking it therein by means of two screws 1330, for example. The end effector frame 1310 may include a dedicated slot 1312 for receiving the shaft 840a such that the bevel gear 830 remains outside the frame 1310 after the insertion module 80 is inserted into the frame 1310, to enable its coupling to the bevel gear 1324 of the motor assembly 1320.

Figure 15B:
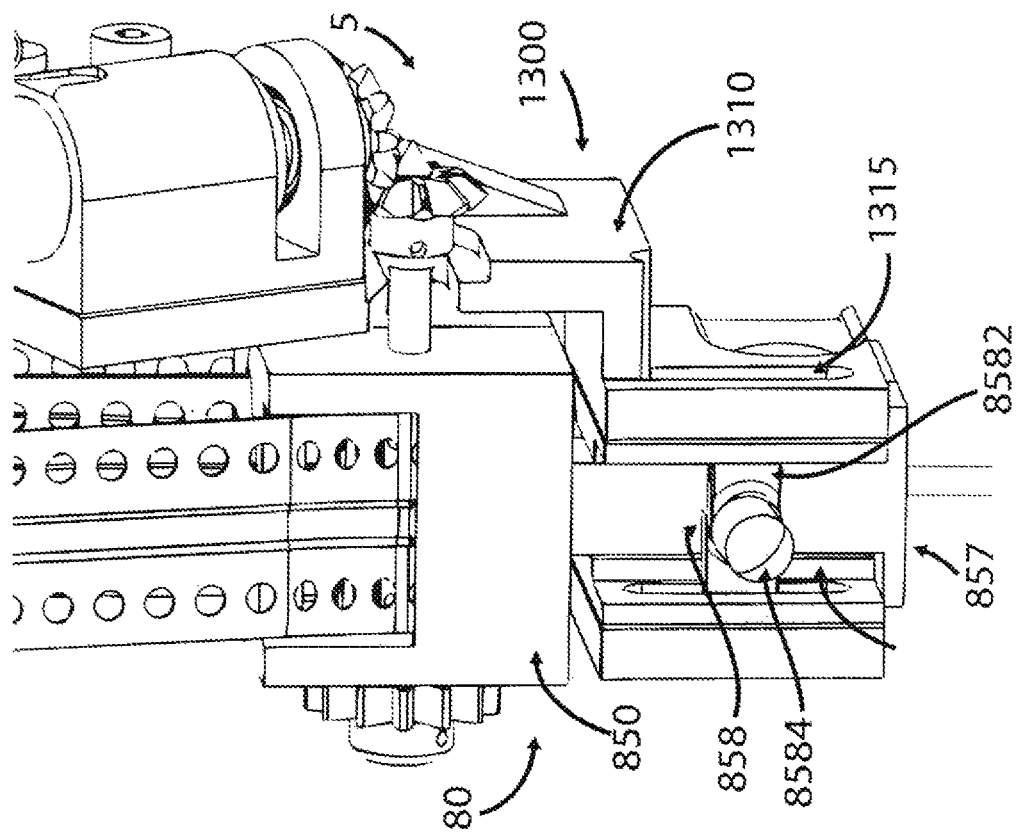
FIGS. 15A-15B are perspective views of an exemplary mechanism for securing the insertion device to the robotic end effector.
Figure 15A:
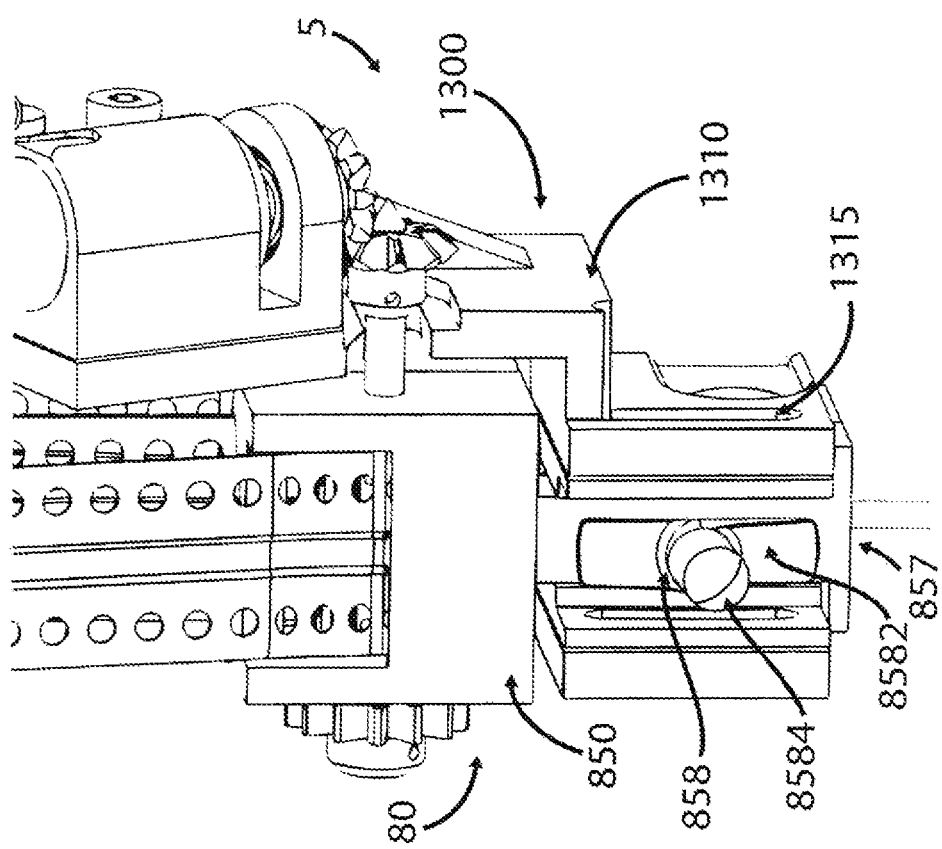

FIGS. 15A-15B show an alternative mechanism for locking the insertion module 80 within the frame 1310 of the end effector 1300. In some implementations, the insertion module's holder 850, or more specifically, the needle guide portion 857 of the holder, may include a rotatable element 858 including two blades 8582 (which may be manufactured as a single long blade), and a knob 8584 which can be grasped by the user. The end effector frame 1310 may have two slits 1315, opposite one another, such that the blades 8582 can enter the slits 1315 when the rotatable element 858 is rotated via the knob 8584. When the rotatable element 858 is in a vertical position, i.e., the blades 8582 are parallel to the needle 800, as shown in FIG. 15A, the insertion module 80 can be moved freely in and out of the end effector frame 1310. When the rotatable element 858 is rotated into a substantially horizontal position, i.e., 90 degrees (or slightly less/more) to the right or to the left, the blades 8582 enter the slits 1315, as shown in FIG. 14B, and the insertion module 80 is locked in its place within the frame 1310 such that it cannot be removed from the end effector 1300 by mere pulling.

Figure 16:
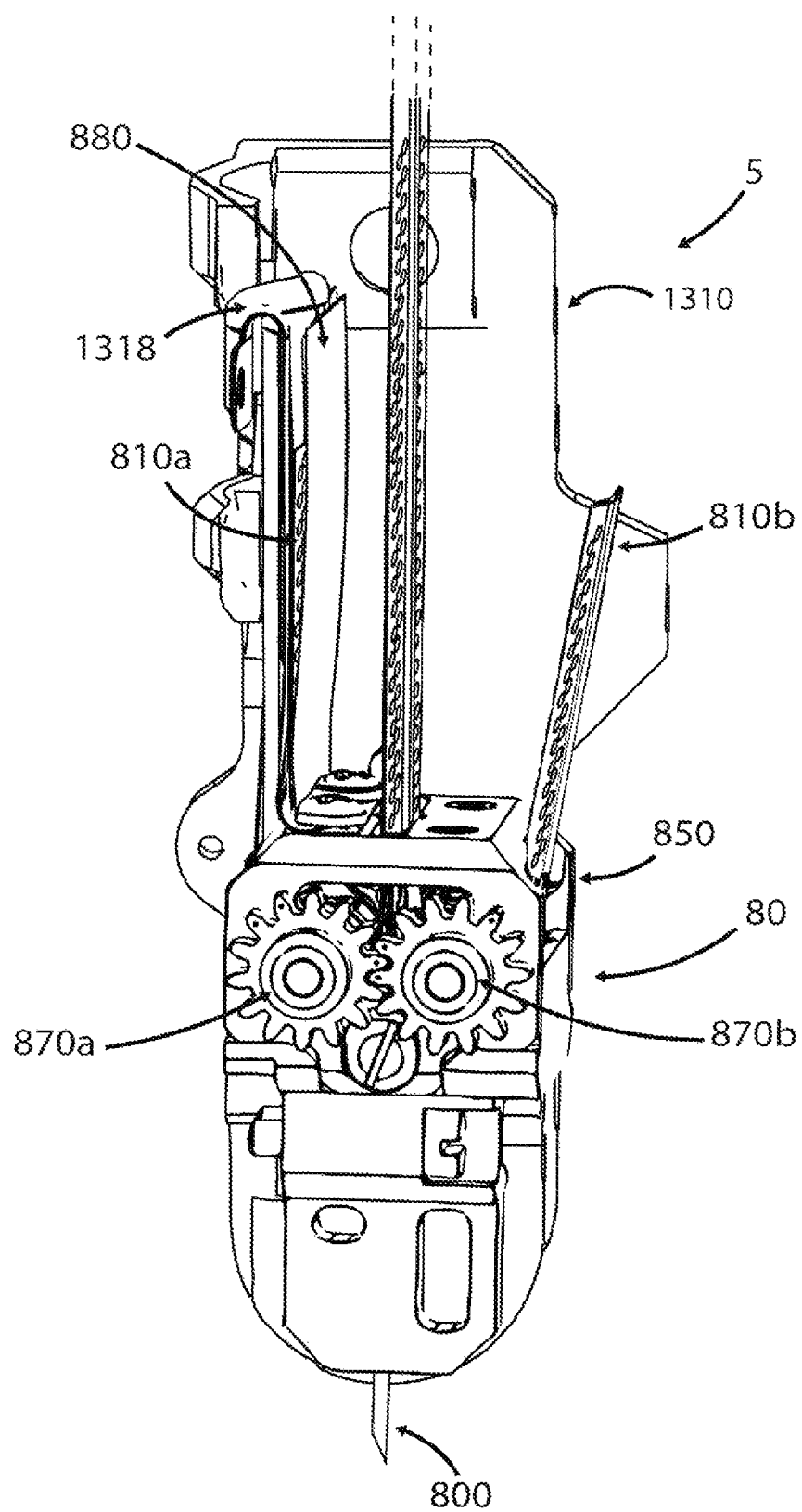
FIG. 16 shows exemplary rear and front guides for controlling the strips' advancement direction.

FIG. 16 shows the insertion module 80 inserted within the end effector frame 1310. As described above, as the rollers 820a, 820b counter-rotate, the protrusions of the rollers engage the perforations of the strips, which causes the strips 810a, 810b to peel off the needle 800 in opposite directions, around the rollers 820*a*, 820*b*, and then exit the insertion module's holder 850. In some implementations, the interface between the insertion assembly 5 and the automated insertion device (not shown) may be such that as the strips 810*a*, 810*b* exit the holder 850 and fold outwardly, at least one of the strips, e.g., strip 810*a*, might contact other components of the automated insertion device, such as a joint (not shown) connecting the end effector to the automated insertion device, which may interfere with its proper function. Thus, in some implementations the frame 1310 of the end effector 1300 may include a back guide 1318 and the insertion module 80 may include a front guide 880 coupled to the holder 850, that together prevent the strip 810*a* from folding outwardly toward the automated insertion device by constraining the strip 810*a* to the space between them. In some implementations, there may be provided only a back guide 1318 without a front guide 880.

Figure 17A:
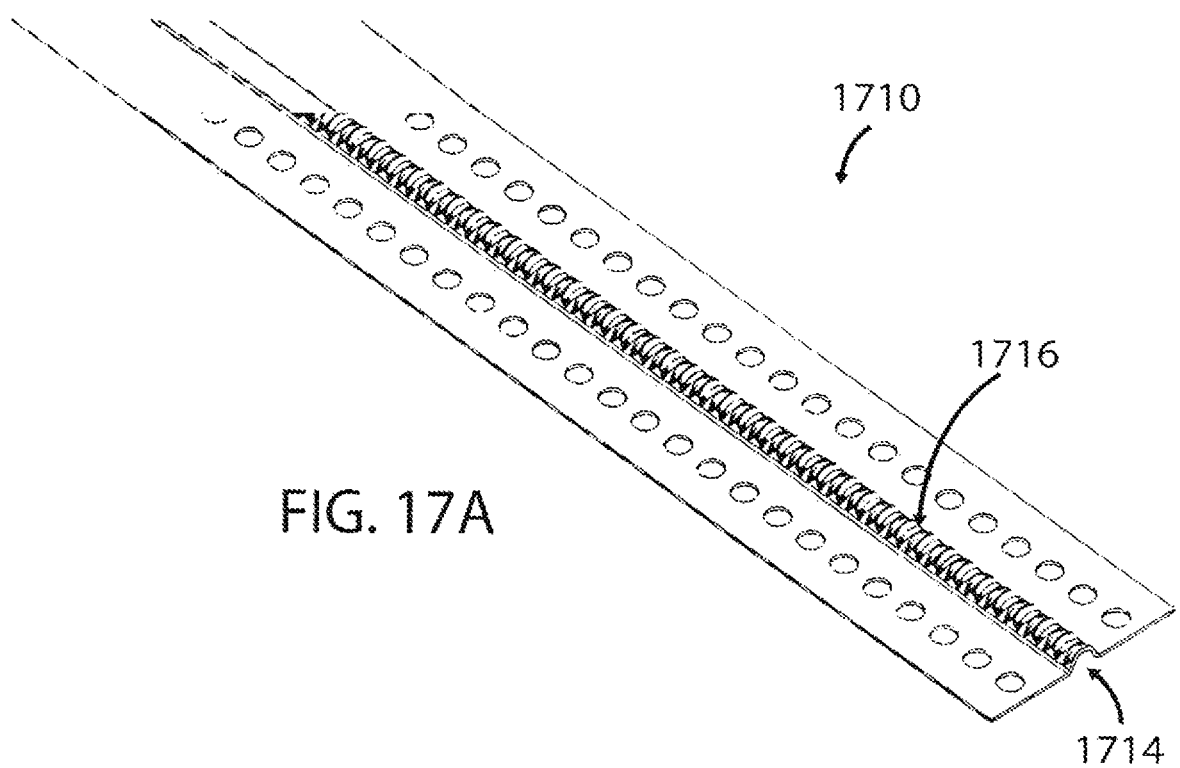
FIGS. 17A-17B show perspective and longitudinal cross-sectional views, respectively, of an exemplary strip having weakened sections along the length of its longitudinal groove.
Figure 17B:
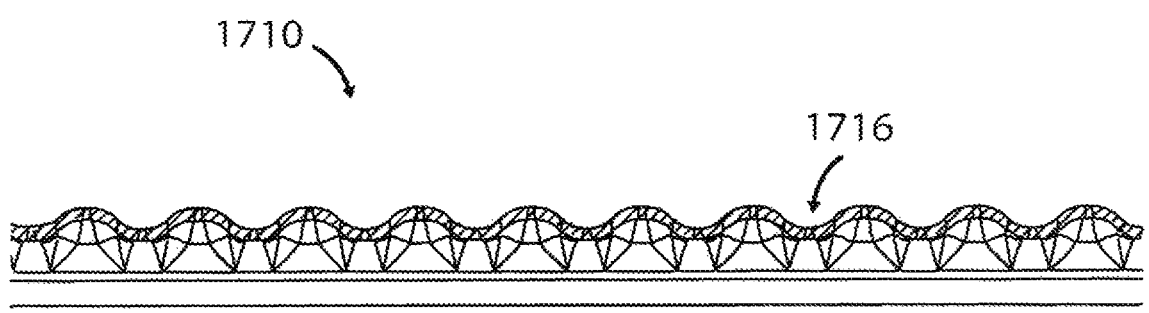

FIG. 17A shows a perspective view of an exemplary strip 1710. As previously discussed, as the rollers counter-rotate, the protrusions of the rollers engage the perforations of the strips, resulting in the strips, with the needle enclosed therebetween, being pulled in the distal direction, while the strips detach from each other and peel off the needle in opposite directions and around the rollers. Since the strips 1710 are not flat but have a groove 1714 running along their length, with the convex side of the groove facing the roller, causing the strips to detach from each other and curve outwardly as they are being pulled by the rotating rollers requires a significant amount of energy, which can only be provided by a powerful and relatively large propulsion mechanism (e.g., motor and gears, piston, etc.). Thus, in order to reduce the amount of energy required to detach the strips from each other and cause them to curve outwardly and wind around the rollers, the strips' groove 1714 may include weakened sections 1716 along its length, which facilitate the curving action of the strips without diminishing the strength of the strips 1710. Preferably, the weakened sections 1716 should be spaced apart according to the natural plastic deformation pattern of the strip 1710, as determined empirically. FIG. 17B is a longitudinal cross-sectional view of the groove 1714 of strip 1710, showing the wave-like profile of the groove 1714 having weakened areas 1716, in this case equally spaced weakened areas 1716.

Once the medical tool (e.g., needle) is inserted into its desired position within the patient's body, the physician/clinician may prefer to remove the insertion device/assembly and the entire automated insertion system (when a body-mounted insertion system is employed) from the patient's body, leaving only the tool in its place. For example, during biopsies in which an introducer is inserted into the patient's body using the insertion device, once the introducer is in its position, the core of the introducer is removed from the introducer and a biopsy needle is inserted through the introducer and into the target (e.g., tumor). In such cases, the insertion device and/or the automated insertion device may obstruct the clinician's view or actions such that he/she may prefer to remove all devices/components other than the introducer from the patient's body.

Figure 18A:
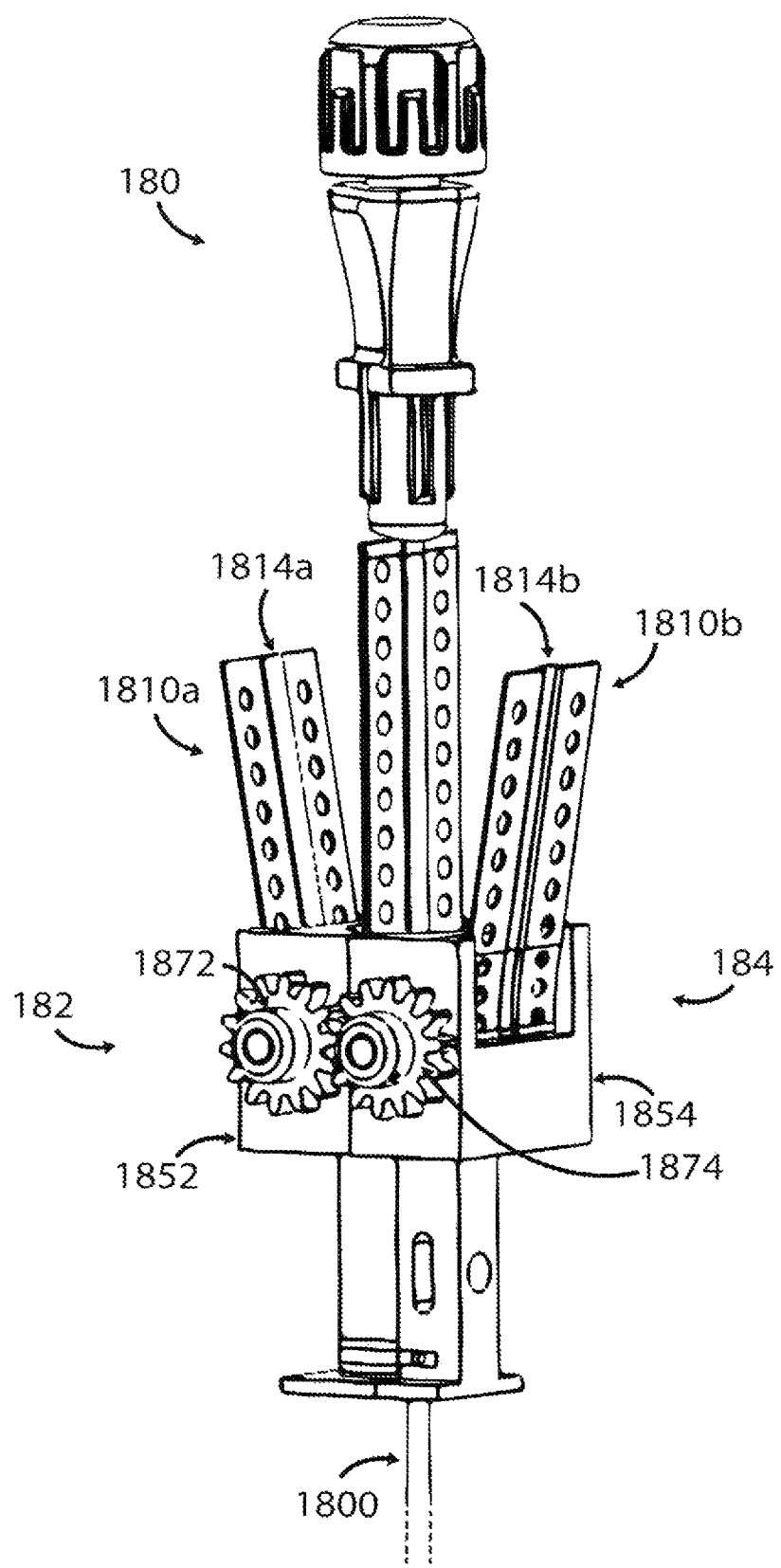
FIGS. 18A-18B show isometric views of an exemplary modular insertion device in assembled (FIG. 18A) and disassembled (FIG. 18B) states.

FIG. 18A shows an isometric view of an exemplary modular insertion device/module 180 in its assembled state. The insertion module comprises two parts 182, 184 connected along their longitudinal axis. Each part 182, 184 includes one portion of the holder 1852, 1854, one strip 1810*a*, 1810*b*, one roller (not shown) and one gear 1872, 1874 (all numerals respectively). In the initial situation for inserting the needle, with the two parts 182, 184 connected, the strips 1810*a*, 1810*b*, in the region before being fed to the rollers, are attached to each other or held together, and their coupled grooves 1814*a*, 1814*b* together form the channel that receives and encloses the needle 1800.

Figure 18B:
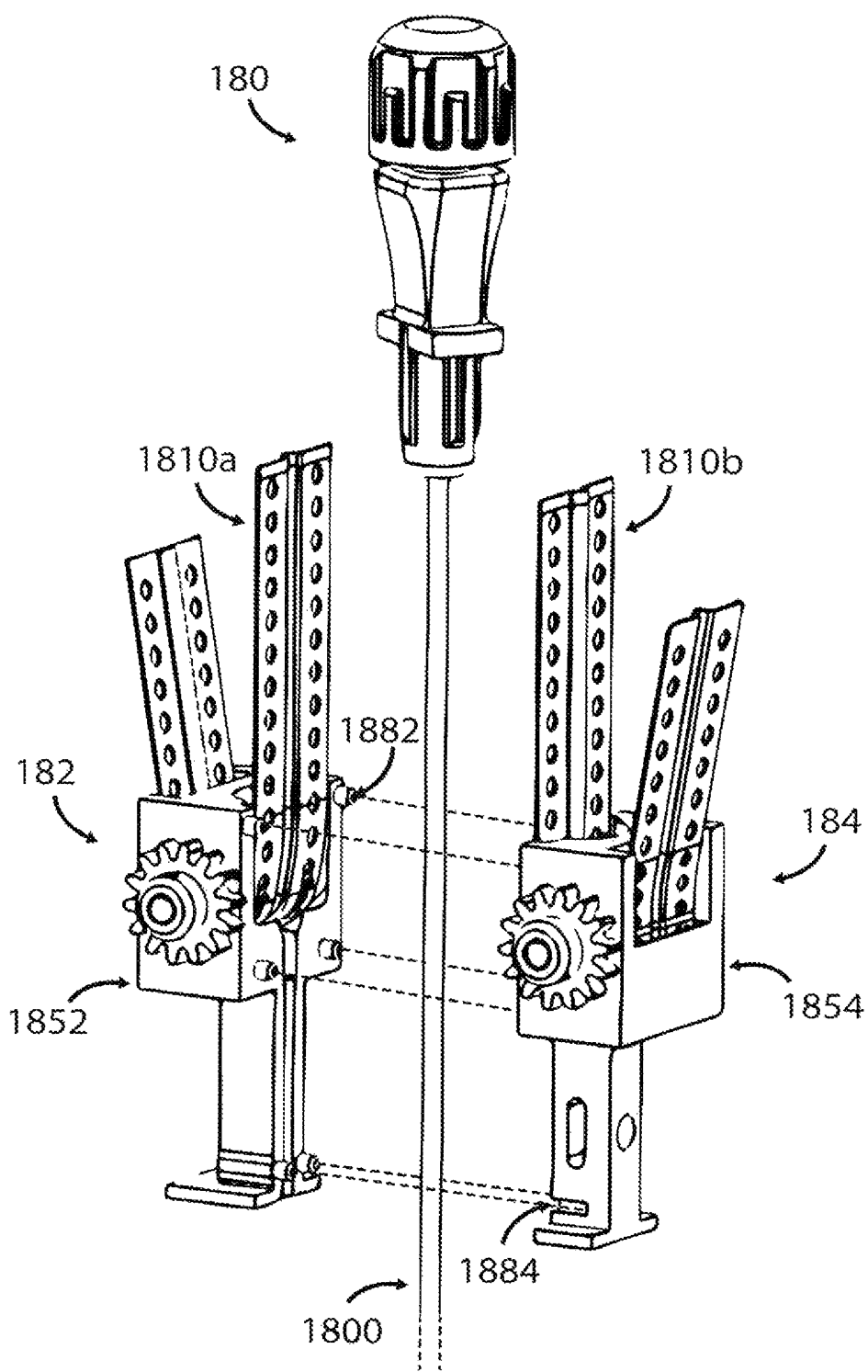

FIG. 18B shows an isometric view of the exemplary modular insertion device/module 180 in its disassembled state. One of the parts, e.g. part 182, may have a plurality of protrusions 1882, and the second part, e.g. part 184, may have a plurality of corresponding slots/niches 1884 (only one slot/niche 1884 is visible in FIG. 18B) for receiving the protrusions 1882 when the two parts 182, 184 are connected. It can be appreciated that any other suitable method for connecting the two parts of the insertion module may be implemented. Since the needle 1800 is enclosed within the channel formed between the strips 1810*a*, 1810*b*, but it is not connected to the strips 1810, 1810*b*, or to any other component of the insertion module 180, once the needle 1800 has reached its target, the user can disconnect the two parts 182, 184 from one another, thus detaching the strips 1810*a*, 1810*b* from one another and away from the needle 1800, without applying on the needle 1800 any major forces which may cause it to move from its position.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

The invention claimed is:

1. An insertion device for insertion of a medical tool towards a target in a body of a subject, the insertion device comprising:

two flexible strips connected to each other along at least a portion of their lengths and having a central channel therebetween configured to receive the medical tool; and two rollers disposed on opposite sides of the connected two flexible strips;

wherein the connected two flexible strips and the medical tool are configured to be secured together at an end remote from the two rollers, upon the medical tool being received within the central channel, such that counter-rotation of the two rollers, in an appropriate direction, moves the connected two flexible strips towards the two rollers, resulting in advancement of the medical tool towards the target; and wherein the insertion device comprises two separate units configured to be connected to and disconnected from each other, each unit comprising one flexible strip of the two flexible strips and one roller of the two rollers.

2. An insertion device according to claim 1, wherein each roller of the two rollers comprises a plurality of protrusions arranged along its circumference, the plurality of protrusions being configured to engage with corresponding plurality of holes formed along the length of each flexible strip of the two flexible strips.

3. An insertion device according to claim 2, wherein the distance between two adjacent protrusions of the plurality of protrusions is larger than the distance between two adjacent holes of the plurality of holes.

4. An insertion device according to claim 1, wherein the two flexible strips are connected to each other on at least one side of the central channel, and are not connected to each other in a region of the central channel.

5. An insertion device according to claim 1, further comprising a holder member configured to secure together the connected two flexible strips and the medical tool at the end remote from the two rollers.

6. An insertion device according to claim 1, further comprising a guide member comprising:
one or more cavities configured to accommodate the two rollers; and
an opening configured to allow passage of the medical tool therethrough.

7. An insertion device according to claim 6, wherein the opening comprises a constraining mechanism configured to be adjusted according to the dimensions of the medical tool, at least a portion of the constraining mechanism being disposed within the opening, wherein the constraining mechanism comprises at least two portions disposed opposite each other, and wherein at least one of the at least two portions is adapted to be moved towards another of the at least two portions.

8. An insertion device according to claim 1, further comprising a separating feature configured to direct each flexible strip of the two flexible strips around a roller of the two rollers, wherein the separating feature comprises at least one of:
(a) unconnected distal ends of the two flexible strips, each of the unconnected distal ends being wound around an associated roller of the two rollers, and
(b) two structural edges, each flexible strip of the two flexible strips being directed by a structural edge of the two structural edges around an associated roller of the two rollers.

9. An insertion device according to claim 1, wherein the central channel includes weakened sections along its length to facilitate winding of each flexible strip of the two flexibles strip around a roller of the two rollers.

10. An insertion device according to claim 1, wherein the medical tool comprises a tip, and the insertion device further comprises a protecting element configured to prevent the tip from contacting an internal surface of the central channel as the medical tool is advanced in the direction of the target.

11. An insertion device according to claim 1, further comprising an encoder configured to determine the position of the medical tool.

12. An insertion device according to claim 1, wherein the medical tool comprises one or more of: a needle, a cannula, a catheter, an introducer, a port, a fluid delivery tube or an electrode rod.

13. An insertion device according to claim 1, wherein each roller of the two rollers comprises two rollers assembled on a single shaft.

14. An insertion system for insertion of a medical tool towards a target in a body of a subject, the insertion system comprising:
an insertion device comprising:
two flexible strips connected to each other along at least a portion of their lengths and having a central channel therebetween configured to receive the medical tool; and
two rollers disposed on opposite sides of the connected two flexible strips;
wherein the connected two flexible strips and the medical tool are configured to be secured together at an end remote from the two rollers, upon the medical tool being received within the central channel, such that counter-rotation of the two rollers, in an appropriate direction, moves the connected two flexible strips towards the two rollers, resulting in advancement of the medical tool towards an insertion target;
a housing configured to receive the insertion device;
a locking mechanism configured to lock the insertion device within the housing; and
an actuation mechanism configured to counter-rotate the two rollers, the actuation mechanism comprising at least one motor and at least one gear.

15. An insertion system according to claim 14, wherein a first portion of the actuation mechanism is coupled to the housing, and a second portion of the actuation mechanism is coupled to a guide member of the insertion device.

16. An insertion system according to claim 14, wherein the locking mechanism comprises:
a rotating member coupled to the insertion device; and
one or more slits formed in the housing;
wherein rotation of the rotating member such that at least a portion of the rotating member enters at least one of the one or more slits locks the insertion device within the housing.

17. An insertion system according claim 14, further comprising:
a front leading element coupled to the insertion device; and
a back leading element coupled to the housing;
wherein the front and back leading elements are configured to receive therebetween an unconnected end of a flexible strip of the two flexible strips after the unconnected end is wound around a roller of the two rollers.

18. An insertion system according to claim 14, wherein each roller of the two rollers comprises a plurality of protrusions arranged along its circumference, the plurality of protrusions being configured to engage with corresponding plurality of holes formed along the length of each flexible strip of the two flexible strips.

19. An insertion system according to claim 14, wherein the medical tool comprises one or more of: a needle, a cannula, a catheter, an introducer, a port, a fluid delivery tube or an electrode rod.

20. An insertion device for insertion of a medical tool towards a target in a body of a subject, the insertion device comprising:
two flexible strips connected to each other along at least a portion of their lengths and having a central channel therebetween configured to receive the medical tool;
two rollers disposed on opposite sides of the connected two flexible strips;
a guide member comprising:
one or more cavities configured to accommodate the two rollers;
an opening configured to allow passage of the medical tool therethrough; and
a constraining mechanism configured to be adjusted according to the dimensions of the medical tool, the constraining mechanism being at least partially disposed within the opening,
wherein the connected two flexible strips and the medical tool are configured to be secured together at an end remote from the two rollers, upon the medical tool being received within the central channel, such that counter-rotation of the two rollers, in an appropriate direction, moves the connected two flexible strips towards the two rollers, resulting in advancement of the medical tool towards the target.

* * * * *